US009180174B2

(12) United States Patent
Matsoukas et al.

(10) Patent No.: US 9,180,174 B2
(45) Date of Patent: Nov. 10, 2015

(54) CONJUGATES COMPRISING MANNAN AND MYELIN OLIGODENTROCYTE GLYCOPROTEIN (MOG)

(75) Inventors: John Matsoukas, Patras (GR); Theodoros Tselios, Mesologgi (GR); Vasso Apostolopoulos, St. Albans (AU); Vivian Tseveleki, Drosia (GR); Maria Katsara, Kalamata (GR); Lesley Probert, Athens (GR)

(73) Assignee: VIANEX S.A., Attikis (GR)

( * ) Notice: Subject to any disclaimer, the term of this patent is extended or adjusted under 35 U.S.C. 154(b) by 367 days.

(21) Appl. No.: 12/864,019

(22) PCT Filed: Jan. 22, 2009

(86) PCT No.: PCT/IB2009/000382
§ 371 (c)(1),
(2), (4) Date: Oct. 28, 2010

(87) PCT Pub. No.: WO2009/093143
PCT Pub. Date: Jul. 30, 2009

(65) Prior Publication Data
US 2011/0243981 A1    Oct. 6, 2011

(30) Foreign Application Priority Data

Jan. 25, 2008 (GB) .................................. 0801424.3
Feb. 8, 2008 (GB) .................................. 0802405.1
Feb. 29, 2008 (GR) .................................. 080100151

(51) Int. Cl.
*A61K 39/00* (2006.01)
*C07K 14/47* (2006.01)

(52) U.S. Cl.
CPC ......... *A61K 39/0008* (2013.01); *C07K 14/4713* (2013.01); *A01K 2207/10* (2013.01); *A01K 2227/105* (2013.01); *A01K 2267/0325* (2013.01); *A61K 2039/6087* (2013.01); *A61K 2039/627* (2013.01)

(58) Field of Classification Search
None
See application file for complete search history.

(56) References Cited

FOREIGN PATENT DOCUMENTS

| WO | WO 02/077025 | 10/2002 |
|---|---|---|
| WO | WO 03/033645 A2 | 4/2003 |
| WO | WO2006093524 A2 | 9/2006 |

OTHER PUBLICATIONS

Anderton, S.M. Immunology. 2001;104:367-376.*
Bielekova, B., et al. Nature Med. 2000;9(10):1167-1175.*
McFarlin, D.E., et al., "Experimental Allergic Encephalomyelitis in the Rat: Response to Encephalitogenic Proteins and Peptides," *Science*, vol. 179, pp. 478-480 (1973).
Acres, B., et al., "MUC1-specific immune responses in human MUC1 transgenic mice immunized with various human MUC1 vaccines," *Cancer Immunol Immunother*, 48, pp. 588-594, (2000).
Apostolopoulos, V. et al., "Aldehyde-mannan antigen complexes target the MHC class I antigen-presentation pathway", *Eur. J. Immunol*, 30, pp. 1714-1723, (2000).
Apostolopoulos, V. et al., "Breast cancer immunotherapy: Current status and future prospects," *Immunology and Cell Biology*, 74, pp. 457-464, (1996).
Apostolopoulos, V. et al., "Cell-mediated immune responses to MUC1 fusion protein coupled to mannan," *Vaccine*, vol. 14. No. 9, pp. 930-938, (1996).
Apostolopoulos, V. et al., "Ex vivo targeting of the macrophage mannose receptor generates anti-tumor CTL responses," *Vaccine*, 18, pp. 3174-3184, (2000).
Bielekova, B., et al., "Encephalitogenic potential of the myelin basic protein peptide (amino acids 83-99) in multiple sclerosis: Results of a phase II clinical trial with an altered peptide ligand," Nature Medicine, vol. 6, No. 10. pp. 1167-1175. (2000).
Davis, W.C. et al., "Use of the Mannan Receptor to Selectively Target Vaccine Antigens for Processing and Antigen Presentation through the MHC Class I and Class II Pathways," *Ann. N.Y. Acad. Sciences*, 969, pp. 119-125, (2002).
Greer, J.M. et al., "Effect of gender on T-cell proliferative responses to myelin proteolipid protein antigens in patients with multiple sclerosis and controls," *Journal of Autoimmunity*, 22, pp. 345-353, (2004).
Greer, J.M. et al., "Increased immunoreactivity to two overlapping peptides of myelin proteolipid protein in multiple sclerosis," *Brain*, 120, pp. 1447-1460, (1997).
Komiyama, Y. et al., "IL-17 Plays an Important Role in the Development of Experimental Autoimmune Encephalomyelitis," The Journal of Immunology, 177, pp. 566-573, (2006).
Kuchroo, V.K. et al., "A Single TCR Antagonist Peptide Inhibits Experimental Allergic Encephalomyelitis Mediated by a Diverse T Cell Repertoire," The Journal of Immunology, 153, pp. 3326-3336. (1994).
Kuchroo, V.K. et al., "Experimental Allergic Encephalomyelitis Mediated by Cloned T Cells Specific for a Synthetic Peptide of Myelin Proteolipid Protein," The Journal of Immunology, vol. 148, pp. 3776-3782. (1992).

(Continued)

*Primary Examiner* — Gerald R Ewoldt
(74) *Attorney, Agent, or Firm* — Brinks Gilson & Lione

(57) ABSTRACT

A first aspect of the invention relates to a conjugate including mannan and at least one epitope comprising a peptide fragment of a protein selected from myelin basic protein (MBP), myelin oligodentrocyte glycoprotein (MOG) and proteolipid protein (PLP), said peptide fragment being in linear or cyclic form; and wherein said epitope is linked to mannan via a [(Lys-Gly)$_n$] bridge, where n is an integer from 1 to 10.

Further aspects of the invention relate to pharmaceutical compositions comprising said conjugates, and their use in the preparation of a medicament for treating an immune disorder.

15 Claims, 8 Drawing Sheets

(56) References Cited

OTHER PUBLICATIONS

Lees, C.J. et al., "Cytokine Production from Murine CD4 and CD8 Cells After Mannan-MUC1 Immunization," Journal of Interferon and Cytokine Research, 19, pp. 1373-1379. (1999).
Lees, C.J. et al., "Immunotherapy with mannan-MUC1 and IL-12 in MUC1 transgenic mice," Vaccine, 19, pp. 158-162. (2001).
Lees, C.J. et al., "The effect of T1 and T2 cytokines on the cytotoxic T cell response to mannan-MUC1," Cancer Immunol. Immunother., 48, pp. 644-652. (2000).
Linington, C. et al., "Augmentation of Demyelination in Rat Acute Allergic Encephalomyelitis by Circulating Mouse Monoclonal Antibodies Directed Against a Myelin/Oligodendrocyte Glycoprotein," American Journal of Pathology, vol. 130, No. 3, pp. 443-454. (1988).
Mantzourani, E.D. et al., "Structural Requirements for Binding of Myelin Basic Protein (MBP) Peptides to MHC II: Effects on Immune Regulation," Current Medicinal Chemistry, 12, pp. 1521-1535. (2005).
Mantzourani, E.D. et al., "A putative bioactive conformation for the altered peptide ligand of myelin basic protein and inhibitor of experimental autoimmune encephalomyelitis," Journal of Molecular Graphics and Modelling, 25, pp. 17-29. (2006).
Mantzourani, E.D. et al., "Comparison of Proposed Putative Active Conformations of Myelin Basic Protein Epitope 87-99 Linear Altered Peptide Ligands by Spectroscopic and Modelling Studies: The Role of Positions 91 and 96 in T-Cell Receptor Activation," J. Med. Chem., 49, pp. 6683-6691. (2006).
Mantzourani, E.D. et al., "Molecular dynamics at the receptor level of immunodominant myelin basic protein epitope 87-99 implicated in multiple sclerosis and its antagonists altered peptide ligands: Triggering of immune response," Journal of Molecular Graphics and Modelling, 26, pp. 471-481. (2007).
Martin, R. et al., "Immunological Aspects of Demyelinating Diseases," Annu. Rev. Immunol. 10, pp. 153-187. (1992).
Matsoukas, J., et al., "Design and Synthesis of a Novel Potent Myelin Basic Protein Epitope 87-99 Cyclic Analogue: Enhanced Stability and Biological Properties of Mimics Render them a Potentially New Class of Immunomodulators," J. Med. Chem., 48, pp. 1470-1480. (2005).
Mendel, I., et al., "A myelin oligodendrocyte glycoprotein peptide includes typical chronic experimental autoimmune encephalomyelitis in H-2b mice: fine specificity and T cell receptor Vβ expression of encephalitogenic T cells," Eur. J. Immunol, 25, pp. 1951-1959. (1995).
Singh, R.A.K., et al., "Differential Activation of ERK, p. 38, and JNK Required for Th1 and Th2 Deviation in Myelin-Reactive T Cells Inducted by Altered Peptide Ligand," The Journal of Immunology, 173, pp. 7299-7307. (2004).
Steinman, L., "Multiple Sclerosis: A Coordinated Immunological Attack against Myelin in the Central Nervous System," Cell, vol. 86, pp. 299-302. (1996).
Sutton, C. et al., "A crucial role for interleukin (IL)-1 in the induction of IL-17—producting T cells that mediate autoimmune encephalomyelitis," JEM, vol. 203, No. 7, pp. 1685-1691. (2006).
Trotter, J. L., et al., "T cell recognition of myelin proteolipid protein and myelin proteolipid protein peptides in the peripheral blood of multiple sclerosis and control subjects," Journal of Neuroimmunology, 84, pp. 172-178. (1998).
Tselios, T., et al., "Antagonistic Effects of Human Cyclic MBP 87-99 Altered Peptide Ligands in Experimental Allergic Encephalomyelitis and Human T-Cell Proliferation," J. Med. Chem., 45, pp. 275-283. (2002).
Tselios, T., et al., "Design and Synthesis of a Potent Cyclic Analogue of the Myelin Basic Protein Epitope MBP 72-85: Importance of the Ala 81 carboxyl Group and of a Cyclic conformation for Induction of Experimental Allergic Encephalomyelitis," J. Med. Chem., 42, pp. 1170-1177. (1999).
Tselios, T., et al., "Synthesis and study of the electrophoretic behavior of mannan conjugates with cyclic peptide analogue of myelin basic protein using lysine-glycine linker," Analytical Biochemistry 347, pp. 121-128. (2005).
Tselios, T., et al., "Treatment of Experimental Allergic Encephalomyelitis (EAE) Induced by Guinea Pig Myelin Basic Protein Epitope 72-85 with a Human MBP 87-99 Analogue and Effects of Cyclic Peptides," Bioorganic & Medicinal Chemistry, 8, pp. 1903-1909. (2000).
Tselios, T., et al., "Treatment of Experimental Allergic Encephalomyelitis (EAE) by a Rationally Designed Cyclic Analogue of Myelin Basic Protein (MBP) Epitope 72-85," Bioorganic & Medicinal Chemistry Letters 10, pp. 2713-2717. (2000).
Tsuchida, T., et al., "Autoreactive CD8+ T-cell responses to human myelin protein-derived peptides," Immunology, vol. 91, pp. 10859-10863. (1994).
Vaughan, H.A., et al., "Induction of humoral and cellular responses in cynomolgus monkeys immunized with mannan-human MUC1 conjugates," Vaccine, 17, pp. 2740-2752. (1999).
Vaughan, H.A., et al., "The immune response of mice and cynomolgus monkeys to macaque mucin 1-mannan," Vaccine, 18, pp. 3297-3309. (2000).
Zamvil, S.S., et al., "The T Lymphocyte in Experimental Allergic Encephalomyelitis," Annu. Rev. Immunol., 8, pp. 579-621. (1990).
Vasso Apostolopoulos, Geoffrey A. Pietersz, Bruce E. Loveland, Mauro S. Sandrin, and Ian F. C. Mckenzie, "Oxidative/Reductive Conjugation of Mannan to Antigen Selects for $T_1$ or $T_2$ Immune Responses," Proc. Natl. Acad. Sci. USA, vol. 92 pp. 10128-10132 (Oct. 1995).
Constantinescu CS, Farooqi N, O'Brien K, Gran B., "Experimental Autoimmune Encephalomyelitis (EAE) As a Model for Multiple Sclerosis (MS)," Br J Pharmacal, 164(4):1079-106 (Oct. 2011).
Richard K. Burt, Josette Padilla, Wendy Smith Begolka, Mauro C. Dal Canto and Stephen D. Miller, "Effect of Disease Stage on Clinical Outcome After Syngeneic Bone Marrow Encephalomyelitis Transplantation for Relapsing Experimental Autoimmune," http://bloodjournal.hematologylibrary.org/, Jan. 16, 2014.
Manmohan Singhal and Parul Srivastava, "Experimental Autoimmune Encephalomyelitis Model for Discovery of New Therapy for Multiple Sclerosis," Global Journal of Pharmacology, 6 (3): 208-215 (2012).
Khan N, Smith MT, "Multiple Sclerosis-Induced Neuropathic Pain: Pharmacological Management and Pathophysiological Insights From Rodent EAE Models," Inflammopharmacology. Nov. 14, 2013. [Epub ahead of print; http://www.ncbi.nlm.nih.gov/pubmed/24234347]].
McCarthy DP, Richards MH, and Miller SO, Mouse Models of Multiple Sclerosis: "Experimental Autoimmune Encephalomyelitis and Theiler's Virus-Induced Demyelinating Disease," Methods Mol Biol., 900:381-401 (2012).
Kappos L et al., "Induction of a non-encephalitogenic type 2 T helper-cell autoimmune response in multiple sclerosis after administration of an altered peptide ligand in a placebo-controlled, randomized phase II trial," Nature Medicine, 6:10, pp1176-1182 (Oct. 2000).
Deraos GN et al., "Design and Synthesis of Myelin Basic Protein (MBP) linear and cyclic peptide analogues complexed with Mannan. Effect in cytokine production," 29th European Peptide Symposium, GDANSK, Poland, Sep. 3-8, 2006, Edited by K. Rolka, P. Rekowski and J. Silberring.
Katsara M et al., "Design of novel cyclic altered peptide ligands of myelin basic protein $MBP_{83-99}$ that modulate immune responses I SJL/J mice," J Med Chem, 51(13):3971-3978 (2008).
Katsara M et al., "Mannosylation of mutated $MBP_{83-99}$ peptides diverts immune responses from Th1 to Th2," Mol. Immunol, 45(13): 3661-3670 (2008).
Tseveleki, et al., "Immunotherapy of experimental autoimmune encephalomyelitis using APC-targeted myelin peptides as prophylactic and therapeutic vaccines," Laboratory of Molecular Genetics, Hellenic Pasteur Institute, Athens, Greece, 11th International Congress in Neuroimmunology (2012).

* cited by examiner

| Sample type | S. Cord inflammation | S. cord demyelination | Brain inflammation | Brain demyelination |
|---|---|---|---|---|
| PBS-control | 3,5 | 1 + Vac | ubi + | 0 |
| PBS-control | 1,5 | 1 | ubi + | 1 |
| PBS-control | 3,6 | 3 | Cer + | 1 |
| PBS-control | 2,8 | 2 | Cer + | 0 |
| OxMan MOG | 0,2 | 0 | 0 | 0 |
| OxMan MOG | 0,1 | 0 | 0 | 0 |
| OxMan MOG | 0,2 | 0 | 0 | 0 |
| OxMan MOG | 0 | 0 | 0 | 0 |
| OxMan MOG | 0,3 | 0 | Cer + | 0 |
| OxMan MOG | 0,2 | 1 | Cer + | 0 |
| RedMan MOG | 0,1 | 0 | 0 | 0 |
| RedMan MOG | 1,1 | 1 | Cer + | 1 |
| RedMan MOG | 1,8 | 1 + Vac | Men | 0 |
| RedMan MOG | global hypoxia | global hypoxia | global hypoxia | global hypoxia |
| RedMan MOG | 1,8 | 1 + Vac | Cer + | 0 |
| RedMan MOG | 1,7 | 0,5 + Vac | Cer + | 0,5 |
| Alone OxMan | 1,6 | 1 | ubi + | 0,5 |
| Alone OxMan | 1,8 | 0,5 | Cer + | 0 |
| Alone OxMan | 1,5 | 0,5 | Men | 0 |
| Alone OxMan | 2,6 | 2 | Cer + | 0,5 |
| Alone OxMan | 2,2 | 1 | ubi + | 0 |
| Alone RedMan | 0,2 | 0 | 0 | 0 |
| Alone RedMan | 1,8 | 0,5 | ubi + | 0 |
| Alone RedMan | 2 | 1 | Men | 0 |
| Alone RedMan | 4,4 | 2 | ubi + | 1 |
| MOG alone | 1,6 | 2 | ubi + | 0,5 |
| MOG alone | 2,1 | 2 | ubi + | 0,5 |
| MOG alone | 2 | 0,5 | Cer + | 0,5 |
| MOG alone | 1,7 | 1 | Cer + | 0,5 |
| MOG alone | 1 | 2 | ubi + | 1 |
| MOG alone | 2,7 | 2 | ubi + | 1 |
| Control 1 | 0,8 | 1 | ubi + | 0,5 |
| Control 2 | 3,2 | 2 | ubi + | 1 |
| Control 3 | 2,3 | 2 | ubi + | 1 |

CONJUGATES COMPRISING MANNAN AND MYELIN OLIGODENTROCYTE GLYCOPROTEIN (MOG)

CROSS REFERENCE TO RELATED APPLICATIONS

This application claims priority to PCT/IB2009/000382, filed Jan. 22, 2009, which application claims priority to GB 0801424.3, filed Jan. 25, 2008, GB 0802405.1, filed Feb. 8, 2008, and GR 20080100151, filed Feb. 29, 2008.

FIELD OF THE INVENTION

The present invention relates to conjugates of myelin antigens that are useful candidates for the immunotherapy of multiple sclerosis (MS).

BACKGROUND TO THE INVENTION

Multiple sclerosis (MS) is a chronic disease of the central nervous system (CNS) characterized by local T cell and macrophage infiltrates, demyelination and loss of neurologic function [Steinman, 1996; Martin, et al., 1992; Mantzourani et al., 2005]. MS is an autoimmune disease triggered by CNS-specific CD4+ T lymphocytes. Candidate autoantigens include constituents of the myelin sheath, such as myelin basic protein (MBP), proteolipid protein (PLP) and myelin oligodendrocyte glycoprotein (MOG).

An association between major histocompatibility complex (MHC) class II alleles and disease has been observed in MS patients, in particular HLA-DR1, HLA-DR2 and HLA-DR4. Although the pathology of MS remains unclear, there is evidence that T cells recognizing encephalitogenic epitopes of myelin, such as MBP, play a pathogenic role in the induction of MS. Studies have shown that T cell responses in patients are associated with the recognition of the 81-105 region of MBP (QDENPVVHFFKNIVTPRTPPPSQGK; SEQ ID NO. 4), and with highest affinity and binding to HLA-DR2 for the peptide epitope $MBP_{83-99}$ (ENPVVHFFKNIVTPRTP; SEQ ID NO. 1). T cell recognition of this region of MBP has also been shown in healthy individuals, although at relatively low precursor frequencies. The binding of $MBP_{83-99}$ to HLA-DR2 is via hydrophobic $V^{87}$ and $F^{90}$ residues, whilst, $H^{88}$, $F^{89}$, and $K^{91}$ are TCR contact residues [Mantzourani et al., 2005].

The pathogenic role of autoimmune T cells recognizing encephalitogenic epitopes of MBP has also been noted in experimental autoimmune encephalomyelitis (EAE), one of the best-studied experimental animal models of MS. EAE represents an invaluable in vivo system for the evaluation of therapeutic approaches. EAE is induced in susceptible animals by immunodominant epitopes of the myelin sheath. Similar clinical and histopathological features to MS can be induced in susceptible mouse strains by immunization of myelin components. EAE is mediated by CD4+ T cells of the Th1 phenotype (IFN-γ). Like MS, EAE susceptibility is dependent on the MHC background of the mouse and different peptides are immunogenic and induce EAE in different strains. Myelin Oligodendrocyte Glycoprotein (MOG) residue 35-55 induces chronic (non-relapsing) EAE in C57BL/6 mice, guinea pig MBP residue 74-85 induces acute (relapsing-remitting) EAE in Lewis rats and proteolipid protein (PLP) residue 139-151 induces acute EAE in SJL/J mice [Zamvil et al., 1990].

The SJL/J mouse strain (H-2$^s$ haplotype) is commonly used for EAE since numerous histopathological, clinical and immunological features resemble that of human MS compared to other mouse or rat strains. In the SJL/J mouse strain, residues from the encephalitogenic epitope $MBP_{81-100}$ have been shown to bind with high affinity. In fact, the minimum epitope required for binding is $MBP_{83-99}$. Furthermore, in SJL/J mice, CD4 T cell responses to PLP residues 139-151 ($PLP_{139-151}$: sequence HSLGKWLGHPDKF; SEQ ID NO. 3) is qualitatively different from responses to encephalitogenic of $MBP_{83-99}$ in that the PLP peptide-specific clones are heterogeneous. As a first step toward understanding the cellular and molecular basis and the biologic relevance of this heterogeneity, studies have determined whether multiple overlapping epitopes within the $PLP_{139-151}$ are responsible for the diversity. Initial studies demonstrated that the panel of T cell clones reacted with overlapping PLP peptides only when the peptides contained residue 144, thereby suggesting that this is an important site for the activation of all of the clones [Kuchroo, et al., 1992]. Furthermore, $W^{144}$ is the dominant TCR contact residue, as substitution at position 144 with, alanine (A), or other hydrophobic residues, such as phenylalanine (F), abolishes the in vitro stimulatory activity of the peptide and such analogues do not induce EAE [Kuchroo, et al., 1992]. The single TCR antagonist peptide analogue ($L^{144}/R^{147}$), in which both of the major TCR contact residues are substituted, showed the maximum antagonist activity ($L^{144}/R^{147}$), in vitro and also gave the best inhibition of EAE [Kuchroo, et al., 1994].

In the C57BL/6 mouse strain, residues 35-55 from MOG protein have been found to be encephalitogenic [McFarlin, et al., 1973]. Disease is elicited by immunization with $MOG_{35-55}$, resulting in a CD4+ T helper-1 (Th1)-cell response that attacks the myelinated areas of CNS [Zamvil and Steinman, 1990]. T cells supported by monocytes and activated microglial cells mediate inflammation and demyelination. B cells and antibodies are not critical for EAE induction in mice, although antibodies that bind to epitopes of $MOG_{35-55}$ enhance demyelination in some models [Linington, et al., 1988]. In Lewis rats, epitope $MBP_{74-85}$ has been identified as immunodominant for EAE induction. Moreover, peptide analogues based on the human $MBP_{83-99}$ epitope have been found to suppress the EAE symptoms induced from the encephalitogenic $MBP_{74-85}$ epitope. [Mendel et al., 1995; Tselios et al., 1999; Tselios et al., 2000a; Tselios et al., 2000b].

In the light of the above, the peptides $MOG_{35-55}$, $PLP_{139-151}$, $MBP_{74-85}$ and $MBP_{83-99}$ and their head to tail cyclic counterparts clearly represent a promising starting point for the design of altered peptide ligands and peptide analogues, which could be used to alter T cell responses in these animal models and thus lead to new therapeutic approaches against MS and other autoimmune diseases. Moreover, epitopes of MBP, PLP and MOG from multiple sclerosis patients, $MBP_{82-100}$, [Ala$^{86}$]$MBP_{83-99}$, [Ala$^8$]$MBP_{83-99}$, [Tyr$^{89}$]$MBP_{83-99}$, $MBP_{110-118}$, $MOG_{97-108}$, $PLP_{97-117}$, $PLP_{185-206}$, $PLP_{40-60}$, $PLP_{190-209}$, $PLP_{184-199}$, $PLP_{80-88}$, $PLP_{30-49}$, $PLP_{180-199}$ and the like are recognized/presented by T cells/B cells from the peripheral blood of MS patients or are able to induce peptide-specific T cells responses in individuals [Greer, et al., 1997, Singh, et al., 2004, Greer, et al., 2004, Tsuchida, et al., 1994, Trotter, et al., 1998].

Current Peptide Therapies for MS

Current peptide therapies of MS include treatment with interferons (interferon beta-1α and interferon beta-1(3) and glatiramer acetate (copolymer-1) which is a synthetic protein comprised of the major amino acids Glu, Gln, Lys, Arg of MBP. These immunomodulators have been approved by the FDA for patients with relapsing-remitting MS. Interferons given by subcutaneous injection reduce the frequency, severity and duration of exacerbation, but their impact on preventing long term disability has not yet been established. In addition, side effects are common and consist of reactions at the injection site, fever, myalgia and flu-like syndrome. So far the reported benefits from the use of interferons and copolymers are marginal and the need for improved therapeutics is imperative.

Another approach under clinical investigation for autoimmune suppression is the oral administration of autoantigens. Orally administered antigens have been shown to suppress autoimmunity in animal models, including EAE, collagen and adjuvant-induced arthritis, uveitis and diabetes in the non-obese diabetic mouse. Low doses of oral antigen induce antigen-specific regulatory T-cells which act by releasing inhibitory cytokines such as TGF-$\beta$, IL-4, and IL-10 at the target organ. Thus, one can suppress inflammation at a target organ by orally administering an antigen derived from the site of inflammation, even if it is not the target of the autoimmune response. Initial human trials of orally administered antigen have shown positive findings in patients with MS and rheumatoid arthritis. A double-blind, placebo-controlled, phase III multi-centre trial of oral myelin in relapsing-remitting MS patients is in progress, as are phase II clinical trials investigating the oral administration of type II collagen in rheumatoid arthritis, S-antigen in uveitis and insulin in type I diabetes. This promising method allows for oral administration which is advantageous over previous treatments with interferons and copolymer-1. However, issues relating to the peptidic nature and cost of the administered substance renders the non-peptide mimetic approach, even in its infancy, an attractive goal to pursue. In this regard, our cyclic epitopes, which are more stable than their linear epitope counterparts, offer this advantageous property.

The present invention seeks to provide a new approach towards the therapeutic management of MS. More specifically, the invention focuses on the design and use of peptide analogues of disease-associated myelin epitopes to induce peripheral T-cell tolerance.

STATEMENT OF INVENTION

The present invention provides an immunotherapeutic approach in which immunodominant/antigenic peptide analogues of myelin basic protein (MBP), myelin oligodentrocyte glycoprotein (MOG) or proteolipid protein (PLP) are conjugated (each one or as cluster) to oxidized or reduced mannan via a $[Lys-Gly]_n$ bridge for the treatment of multiple sclerosis (MS).

A first aspect of the invention relates to a conjugate comprising:
(i) mannan; and
(ii) at least one epitope comprising a peptide fragment of a protein selected from myelin basic protein (MBP), myelin oligodentrocyte glycoprotein (MOG) and proteolipid protein (PLP), said peptide fragment being in linear or cyclic form;
wherein said epitope is linked to mannan via a $[(Lys-Gly)_n]$ bridge, where n is an integer from 1 to 10.

Glycosylation is a universal characteristic of proteins in nature, which determines their physicochemical and biological properties. Design and synthesis of glycopeptides is a topic of intense research in the last years, since the glyco-part improves the pharmacokinetic characteristics, enhances or alters the biologic activity and can be used as a tool to study the biologic functions.

Without wishing to be bound by theory, it is believed that conjugating the immunodominant epitopes of MBP, PLP and MOG (linear or cyclic) to mannan actively inhibits or prevents disease through the activation of antigen-specific regulatory T cells or by inducing T cell tolerance to self antigens.

A second aspect of the invention relates to a mixture comprising two or more conjugates as defined above.

A third aspect of the invention relates to a pharmaceutical preparation comprising a conjugate or mixture as defined above, and a pharmaceutically acceptable carrier, diluent or excipient.

A fourth aspect of the invention relates to a conjugate or mixture as defined above for use in medicine.

A fifth aspect of the invention relates to the use of a conjugate or mixture as defined above in the preparation of a medicament for treating MS and other immune disorders.

A sixth aspect of the invention relates to a method of treating an immune disorder, said method comprising administering to a subject a conjugate or a mixture as defined above.

A seventh aspect of the invention relates to a method of immunizing a subject against an immune disorder, said method comprising administering to a subject a conjugate or a mixture as defined above.

An eighth aspect of the invention relates to the use of a conjugate as defined above, in an assay for elucidating agents capable of regulating experimental autoimmune encephalomyelitis (EAE) or regulating multiple sclerosis.

A ninth aspect of the invention relates to a process for preparing a conjugate as defined above, said process comprising the steps of:
(i) reacting an epitope comprising a peptide fragment of a protein selected from myelin basic protein (MBP), myelin oligodentrocyte glycoprotein (MOG) and proteolipid protein (PLP), said peptide fragment being in linear or cyclic form, with a peptide bridge $[(Lys-Gly)_n]$, wherein n is an integer from 1 to 10;
(ii) reacting the product formed in step (i) with oxidized mannan; and
(iii) optionally reducing the product formed in step (ii) to form a reduced mannan conjugate.

A tenth aspect of the invention relates to a vaccine comprising a conjugate or mixture as defined above.

An eleventh aspect of the invention relates to a conjugate or a mixture as defined above for the treatment of MS and other immune disorders.

DETAILED DESCRIPTION

The present invention relates to potent peptides (linear or cyclic) of immunodominant epitopes of myelin sheath, MBP, PLP or MOG which are conjugated with oxidized or reduced mannan via a $(Lys-Gly)_n$ spacer. The conjugates are useful in the treatment of EAE and thus have implications in the treatment of MS. For the first time, epitopes of myelin proteins conjugated to oxidized/reduced mannan have been synthesized, via a $(Lys-Gly)_5$ spacer and shown to completely prevent and protect animals from EAE symptoms without the use of an adjuvant. Preferably, the conjugates of the invention are administrated to animals diluted in buffer solution (pH 6.0-9.0). Evidence suggests that conjugating these disease-associated epitopes to oxidized or reduced mannan via a $(Lys-Gly)_n$ linker induces reduced levels of proliferative $CD4^+$ T cells and cytokines.

Experiments have shown that active immunization of animals with oxidized/reduced mannan conjugated peptides confers protection against EAE (the most widely used animal model for human MS). This protection is evident in two different species, using three different models of EAE. One model represents the relapse-remitting form of the disease ($MOG_{35-55}$ in C57BL/6 mice) and the others represent acute monophasic disease followed by complete remission ($MPB_{72-85}$ in Lewis rats or $PLP_{139-151}$ in SJL/J mice). The results indicate that mannan peptide conjugates could potentially be of significant therapeutic value in the treatment of MS.

Conjugate

One aspect of the invention relates to a conjugate comprising:
(i) mannan; and
(ii) at least one epitope, or cyclic counterpart thereof, of a protein selected from myelin basic protein (MBP), myelin oligodentrocyte glycoprotein (MOG) and proteolipid protein (PLP);
wherein said epitope is linked to mannan via a $[(Lys-Gly)_n]$ bridge, where n is an integer from 1 to 10.

More particularly, the invention relates to a conjugate comprising:
(i) mannan; and
(ii) at least one epitope comprising a peptide fragment of a protein selected from myelin basic protein (MBP), myelin oligodentrocyte glycoprotein (MOG) and proteolipid protein (PLP), said peptide fragment being in linear or cyclic form; wherein said epitope is linked to mannan via a $[(Lys-Gly)_n]$ bridge, where n is an integer from 1 to 10.

As used herein, the term "epitope" refers to a molecular region on the surface of an antigen that is capable of eliciting an immune response and of combining with the specific antibody produced by such a response.

In the context of the present invention, the term "peptide fragment" refers to an amino acid sequence (or variant thereof) derived from a full length protein. Preferably, the peptide fragment has one or more amino acid residues deleted from the full length protein.

In the context of the present invention, these epitopes are typically derived from, or constitute, specific amino acid fragments of the protein sequences of myelin basic protein (MBP), myelin oligodentrocyte glycoprotein (MOG) and/or proteolipid protein (PLP). The epitopes may be linear or cyclic.

In one preferred embodiment, the epitope comprises a peptide fragment of myelin basic protein (MBP).

More preferably, the epitope comprises a peptide selected from $MBP_{83-99}$, $MBP_{82-101}$, $[Ala^8]MBP_{83-89}$, $[Ala^8]MBP_{83-89}$ $[Tyr^8]MBP_{83-89}$ and $MBP_{110-118}$, and variants thereof, in linear or cyclic form.

Even more preferably, the epitope is a peptide selected from $MBP_{83-99}$, $MBP_{82-101}$, $[Ala^8]MBP_{83-89}$, $[Ala^{88}]MBP_{83-89}$, $[Tyr^8]MBP_{83-89}$ and $MBP_{110-118}$, and variants thereof, in linear or cyclic form.

In one preferred embodiment, the epitope comprises the peptide $MBP_{83-99}$, or a variant thereof. Even more preferably, the epitope is $MBP_{83-99}$, or a variant thereof in linear or cyclic form.

In one particularly preferred embodiment, the epitope corresponds to the peptide sequence SEQ ID NO. 1, or a variant thereof:

[SEQ ID NO. 1]
H-Glu-Asn-Pro-Val-Val-His-Phe-Phe-Lys-Asn-Ile-

Val-Thr-Pro-Arg-Thr-Pro-OH in linear or cyclic form. Preferably, the peptide is in linear form.

In one preferred embodiment, the peptide comprises the amino acid sequence of formula (I),

ENPVVHFFK$^{91}$NIVTP$^{96}$RTP   (I; SEQ ID NO. 5)

wherein at least one of $K^{91}$ and $P^{96}$ is substituted by a natural or unnatural amino acid, wherein said peptide is in linear or cyclic form.

In another preferred embodiment of the invention, the peptide comprises the amino acid sequence of formula (Ia), ENPVVHFFK$^{91}$NIVTP$^{96}$RTP   (Ia; SEQ ID NO. 5)

wherein each of $K^{91}$ and $P^{96}$ is substituted by a natural or unnatural amino acid.

In another preferred embodiment, the peptide consists of the amino acid sequence of formula (Ia), wherein each of $K^{91}$ and $P^{96}$ is substituted by a natural or unnatural amino acid.

In one preferred embodiment, $K^{91}$ is substituted by a natural amino acid.

In one preferred embodiment, $K^{91}$ is substituted by an amino acid selected from A, R, E, F and Y.

In a more preferred embodiment, $K^{91}$ is substituted by an amino acid selected from A, E and Y.

In one highly preferred embodiment, $K^{91}$ is substituted by the amino acid Y.

In one preferred embodiment, $P^{96}$ is substituted by a natural amino acid.

In one particularly preferred embodiment, $P^{96}$ is substituted by the amino acid A.

In one especially preferred embodiment, $K^{91}$ is substituted by an amino acid selected from A, R, E, F and Y and $P^{96}$ is substituted by the amino acid A.

In one preferred embodiment, $K^{91}$ is substituted by the amino acid R and $P^{96}$ is substituted by the amino acid A.

In another preferred embodiment, $K^{91}$ is substituted by the amino acid A and $P^{96}$ is substituted by the amino acid A.

In one particularly preferred embodiment, the peptide of the invention is selected from the following sequences:

[$R^{91}$, $A^{96}$]$MBP_{83-99}$   ENPVVHFFRNIVTARTP   (SEQ ID NO. 12)

[$A^{91}$, $A^{96}$]$MBP_{83-99}$   ENPVVHFFANIVTARTP   (SEQ ID NO. 13)

[$A^{91}$,$A^9$]$MBP_{83-99}$ is particularly preferred.

In another preferred embodiment, the peptide comprises the amino acid sequence of formula (Ib), ENPVVHFFK$^{91}$NIVTP$^{96}$RTP   (Ib; SEQ ID NO. 14)

wherein at least one of $K^{91}$ and $P^{96}$ is substituted by an amino acid selected from R, E, F and Y.

In another preferred embodiment, the peptide consists of the amino acid sequence of formula (Ib), wherein at least one of $K^{91}$ and $P^{96}$ is substituted by an amino acid selected from R, E, F and Y.

In one highly preferred embodiment, $K^{91}$ is substituted by an amino acid selected from R, E, F and Y.

More preferably still, the peptide of formula (Ib) is selected from the following:

[$E^{91}$]$MBP_{83-99}$   ENPVVHFFENIVTPRTP   (SEQ ID NO. 15)

[$F^{91}$]$MBP_{83-99}$   ENPVVHFFFNIVTPRTP   (SEQ ID NO. 16)

[$Y^{91}$]$MBP_{83-99}$   ENPVVHFFYNIVTPRTP   (SEQ ID NO. 17)

Peptide [Y$^{91}$]MBP$_{83-99}$ is particularly preferred, linear or cyclic.

Preferably, the peptide of formula (Ia) or (Ib) is a linear peptide

In another preferred embodiment of the invention, the peptide is a cyclic peptide comprising the amino acid sequence of formula (Ic), ENPVVHFFK$^{91}$NIVTP$^{96}$RTP    (Ic; SEQ ID NO. 5)

or a variant thereof wherein one or two amino acids are substituted by a natural or unnatural amino acid.

Preferably, the peptide consists of the amino acid sequence of formula (Ic) cyclised head to tail.

Preferably, at least one of K$^{91}$ and P$^{96}$ is substituted by a natural or unnatural amino acid.

In one preferred embodiment, one or two amino acids are substituted by an amino acid selected from A, R, E, F, S and Y.

In one preferred embodiment, K$^{91}$ is substituted by an amino acid selected from A, R, E, F and Y.

In one preferred embodiment, P$^{96}$ is substituted by a natural amino acid.

More preferably, P$^{96}$ is substituted by the amino acid A.

In one particularly preferred embodiment, K$^{91}$ is substituted by an amino acid selected from A, R, F, S and Y and P$^{96}$ is substituted by the amino acid A.

More preferably still, the K$^{91}$ residue is substituted by the amino acid A. Thus, in one particularly preferred embodiment, the cyclic analogue is cyclo(83-99)[A$^{91}$]MBP$_{83-99}$, with alanine substitution at position 91 and head-tail cyclization between residues 83-99.

In one particularly preferred embodiment, the cyclic peptide is selected from the following:

In another preferred embodiment of the invention, the peptide comprises the amino acid sequence of formula (IIa), VHFFK$^{91}$NIVTP$^{96}$RTP    (IIa; SEQ ID NO. 24)

wherein K$^{91}$ is substituted by the amino acid A and P$^{96}$ is substituted by the amino acid A, wherein said peptide is in linear form.

In one highly preferred embodiment, the peptide of formula (IIa) consists of the sequence VHFF<u>A</u>NIVT<u>A</u>RTP (SEQ ID NO. 24).

In yet another preferred embodiment of the invention, the peptide comprises the amino acid sequence of formula (IIb), VHFFK$^{91}$NIVTP$^{96}$RTP    (IIb; SEQ ID NO. 24)

wherein K$^{91}$ is substituted by the amino acid A and P$^{96}$ is substituted by the amino acid A, wherein said peptide is in cyclic form.

In one highly preferred embodiment, the peptide of formula (IIb) consists of the sequence VHFF<u>A</u>NIVT<u>A</u>RTP (SEQ ID NO. 24) cyclised head to tail, i.e. cyclization between residues 87-99.

In another preferred embodiment of the invention, the epitope comprises a peptide fragment of myelin oligodentrocyte glycoprotein (MOG) in linear or cyclic form.

Preferably, the epitope comprises a peptide selected from MOG$_{35-55}$ and MOG$_{97-108}$, and variants thereof, in linear or cyclic form.

| peptide analogues | | sequence |
|---|---|---|
| cyclo(83-99)MBP$_{83-89}$ | SEQ ID NO. 1 | cyclo(83-99)E N P V V H F F K N I V T P R T P |
| cyclo(83-99)[A$^{91}$]MBP$_{83-99}$ | SEQ ID NO. 18 | cyclo(83-99)E N P V V H F F <u>A</u> N I V T P R T P |
| cyclo(83-99)[R$^{91}$]MBP$_{83-99}$ | SEQ ID NO. 19 | cyclo(83-99)E N P V V H F F <u>R</u> N I V T P R T P |
| cyclo(83-99)[F$^{91}$]MBP$_{83-99}$ | SEQ ID NO. 15 | cyclo(83-99)E N P V V H F F <u>F</u> N I V T P R T P |
| cyclo(83-99)[Y$^{91}$]MBP$_{83-99}$ | SEQ ID NO. 16 | cyclo(83-99)E N P V V H F F <u>Y</u> N I V T P R T P |
| cyclo(83-99)[E$^{91}$]MBP$_{83-99}$ | SEQ ID NO. 14 | cyclo(83-99)E N P V V H F F <u>E</u> N I V T P R T P |
| cyclo(83-99)[A$^{91}$, A$^{96}$]MBP$_{83-99}$ | SEQ ID NO. 13 | cyclo(83-99)E N P V V H F F <u>A</u> N I V T <u>A</u> R T P |
| cyclo(83-99)[R$^{91}$, A$^{96}$]MBP$_{83-99}$ | SEQ ID NO. 12 | cyclo(83-99)E N P V V H F F <u>R</u> N I V T <u>A</u> R T P |
| cyclo(83-99)[F$^{91}$, A$^{95}$]MBP$_{83-99}$ | SEQ ID NO. 20 | cyclo(83-99)E N P V V H F F <u>F</u> N I V T <u>A</u> R T P |
| cyclo(83-99)[Y$^{91}$, A$^{96}$]MBP$_{83-99}$ | SEQ ID NO. 21 | cyclo(83-99)E N P V V H F F <u>Y</u> N I V T <u>A</u> R T P |
| cyclo(83-99)[S$^{91}$, A$^{96}$]MBP$_{83-99}$ | SEQ ID NO. 22 | cyclo(83-99)E N P V V H F F <u>S</u> N I V T <u>A</u> R T P |

In the above nomenclature, (83-99) denotes the site of cyclisation. For example, amino acid residue 83 is joined to residue 99; i.e. the peptide is cyclised "head-to-tail". Cyclo (83-99)[Y$^{9}$]MBP$_{83-99}$ is particularly preferred.

In another preferred embodiment of the invention, the peptide comprises the amino acid sequence of formula (IIa), VHFFK$^{91}$NIVTP$^{96}$RTP    (IIa; SEQ ID NO. 23)

in linear or cyclic form.

More preferably, the epitope is a peptide selected from MOG$_{35-55}$ and MOG$_{97-108}$, and variants thereof, in linear or cyclic form.

In one preferred embodiment, the epitope comprises the peptide MOG$_{35-55}$, or a variant thereof. More preferably, the epitope is MOG$_{35-55}$, or a variant thereof, in linear or cyclic form.

In one particularly preferred embodiment, the epitope corresponds to the peptide sequence SEQ ID NO. 2, or a variant thereof:

[SEQ ID NO. 2]
H-Met-Glu-Val-Gly-Trp-Tyr-Arg-Pro-Pro-Phe-Ser-

Arg-Val-Val-His-Leu-Tyr-Arg-Asn-Gly-Lys-OH in linear or cyclic form. Preferably, the peptide is in linear form.

In another preferred embodiment of the invention, the epitope comprises a peptide fragment of proteolipid protein (PLP) in linear or cyclic form.

Preferably, the epitope comprises a peptide selected from $PLP_{97-117}$, $PLP_{185-206}$, $PLP_{40-60}$, $PLP_{139-151}$, $PLP_{190-209}$, $PLP_{184-199}$, $PLP_{80-88}$, $PLP_{30-49}$, $PLP_{180-199}$, and variants thereof, in linear or cyclic form.

More preferably, the epitope is a peptide selected from $PLP_{97-117}$, $PLP_{185-206}$, $PLP_{40-60}$, $PLP_{139-151}$, $PLP_{190-209}$, $PLP_{184-199}$, $PLP_{80-88}$, $PLP_{30-49}$, $PLP_{180-199}$, and variants thereof, in linear or cyclic form.

In one preferred embodiment, the epitope comprises the peptide $PLP_{139-151}$, or a variant thereof. Even more preferably, the epitope is $PLP_{139-151}$, or a variant thereof, in linear or cyclic form.

In one particularly preferred embodiment, the epitope corresponds to the peptide sequence SEQ ID NO. 3, or a variant thereof:

[SEQ ID NO. 3]
H-His-Ser-Leu-Gly-Lys-Trp-Leu-Gly-His-Pro-Asp-

Lys-Phe-OH in linear or cyclic form. Preferably, the peptide is in linear form.

As used herein, the term "variant" includes any variation wherein; (a) one or more amino acid residues are replaced by a naturally or non-naturally occurring amino acid residue (b) the order of two or more amino acid residues is reversed, (c) both (a) and (b) are present together, (d) a spacer group is present between any two amino acid residues, (e) one or more amino acid residues are in peptoid form, (f) the (N—C—C) backbone of one or more amino acid residues of the peptide has been modified, or any of (a)-(f) in combination. Preferably, the variants arise from one of (a), (b) or (c).

More preferably, one or two amino acids residues are substituted by one or more other amino acid residues. Even more preferably, one amino acid residue is substituted by another amino acid residue. Preferably, the substitution is homologous.

Homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine, a more detailed list of which appears below. Within each peptide carrier moiety more than one amino acid residue may be modified at a time.

As used herein, amino acids are classified according to the following classes;
basic; H, K, R
acidic; D, E
non-polar; A, F, G, I, L, M, P, V, W
polar; C, N, Q, S, T, Y,
(using the internationally accepted single letter amino acid notation) and homologous and non-homologous substitution is defined using these classes. Thus, homologous substitution is used to refer to substitution from within the same class, whereas non-homologous substitution refers to substitution from a different class or by an unnatural amino acid.

Suitable spacer groups that may be inserted between any two amino acid residues of the carrier moiety include alkyl groups such as methyl, ethyl or propyl groups in addition to amino acid spacers such as glycine or β-alanine residues. A further form of variation, type (e), involving the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134. Type (f) modification may occur by methods such as those described in International Application PCT/GB99/01855.

Within the definition of formula (I) it has been demonstrated that it is preferable for amino acid variation, preferably of type (a) or (b), to occur independently at any position. As mentioned above more than one homologous or non-homologous substitution may occur simultaneously. Further variation may occur by virtue of reversing the sequence of a number of amino acid residues within a sequence.

In one embodiment the replacement amino acid residue is selected from the residues of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, and valine.

The replacement amino acid residue may additionally be selected from unnatural amino acids. Non-natural amino acid derivatives that may be used in the context of the present invention include alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allylglycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilised for the purpose of the discussion above, to indicate the hydrophobic nature of the derivative whereas # has been utilised to indicate the hydrophilic nature of the derivative, #* indicates amphipathic characteristics.

In one particularly preferred embodiment, one amino acid of the peptide sequence is substituted by an alanine residue. Even more preferably, each amino acid residue in turn is substituted by an alanine residue in accordance with routine "alanine scanning".

The peptide of the present invention may comprise amino acids in the L or D form, i.e. one or more residues, preferably all the residues may be in the L or D form.

The conjugate of the invention is linked to mannan via a $[(Lys-Gly)_n]$ bridge, where n is an integer from 1 to 10. Preferably, n is an integer from 1 to 5, and even more preferably, n is 5. In one preferred embodiment, n is from 6 to 10, more preferably, from 7 to 10. In another preferred embodiment, n is from 1 to 4, more preferably, from 1 to 3.

Conjugation occurs via Schiff base formation between the free amino groups of the lysine and oxidized mannan. Reduced mannan conjugates may be prepared by adding a reducing agent (e.g. sodium borohydride) to the oxidized mannan conjugates.

Mannan (poly-mannose) conjugated to MUC1 FP or peptides (MUC1, an antigen found on adenocarcinoma cells) in the oxidized (comprising aldehydes) or in the reduced form (aldehydes reduced to alcohols) generates differential immune responses. Mannan has been used as a successful carrier to target peptides to the mannose receptor, which is predominantly found on macrophage and dendritic cells (DCs). Upon binding, MHC class I or MHC class II presentation of peptides is generated, stimulating either CTL/Ab or Th1/Th2 immune responses. Th1 cytokines released after therapeutic administration are associated with exacerbation of MS. However, Th2 cytokines (such as IL-4 and IL-10) have anti-inflammatory properties and down-regulate Th1 responses. Mannose-antigen leads to 100-10,000 fold enhanced potency to stimulate MHC Class II presentation to T cell [Apostolopoulos, et al., 2000a; Apostolopoulos, et al., 2000b]. Mannan has been investigated extensively for its ability to generate responses in several model systems. Its adjuvant function has been shown to stem from its ability to target the mannose receptor on antigen presenting cells. Mice (inbred or MUC1 transgenic) immunized with mannan-MUC1 protein are protected against a MUC1 expressing tumor challenge, as well as reversing established tumors in mice [Apostolopoulos, et al., 1996; Acres, et al., 2000]. Similar results were observed in MUC1 transgenic mice. Either a Th1 response (IL-2, IFN-γ, IL-12, TNF-α and IgG2a antibodies) or Th2 response (no IFN-γ or IL-12, but significant amounts of IL-4, IL-10 and TGF-β and IgG1 antibodies) is generated depending on the mode of conjugation, and whether the mannan is in an oxidized or reduced state [Lees, et al., 1999; Lees, et al., 2000a; Lees, et al., 2000b]. Other cytokines, IL-5, IL-6, IL-13, IL-15, and IL-18 have also been measured with either oxidized or reduced mannan immunogens. In addition to Th1/Th2 type responses to MUC1 in mice, similar responses have been demonstrated in humans and monkeys [Vaughan, et al., 1999; Vaughan, et al., 2000] with MUC1 protein and to an *Anaplasma marginale* MSP-1 peptide in cows [Davis, et al., 2002]. The use of reduced or oxidized mannan conjugated with $MBP_{83-99}$, $PLP_{139-151}$ or $MOG_{35-55}$ epitopes, and in particular, the use of reduced mannan to further divert immune responses to Th2 when conjugated to MBP peptides, constitutes a promising strategy for the immunotherapy of MS.

In one preferred embodiment of the invention, the mannan is reduced mannan. In another preferred embodiment of the invention, the mannan is oxidised mannan.

In one especially preferred embodiment, more than one epitope is linked to mannan, i.e. multiple epitopes are attached to a single mannan residue. For this embodiment, the epitopes may be the same or different.

Thus, in one particularly preferred embodiment, the conjugate comprises a mixture (or "cocktail") of more than one of said epitopes conjugated to a single mannan residue via a $[(Lys-Gly)_n]$ bridge, where n is an integer from 1 to 10, i.e. the mannan may be conjugated to a plurality of epitopes. As above, the mannan may be oxidised or reduced.

In one highly preferred embodiment, the invention relates to a conjugate comprising:
(i) mannan; and
(ii)(a) an epitope comprising a peptide fragment of myelin basic protein (MBP); and
(ii)(b) an epitope comprising a peptide fragment of myelin oligodentrocyte glycoprotein (MOG); and
(ii)(c) an epitope comprising a peptide fragment of proteolipid protein (PLP); each peptide fragment being in linear or cyclic form;
wherein each epitope is linked to mannan via a $[(Lys-Gly)_n]$ bridge, where n is an integer from 1 to 10.

Another embodiment of the invention relates to a mixture comprising two or more conjugates as defined above. For this embodiment, the two or more conjugates may be the same or different. Moreover, each conjugate may itself comprise one or more epitopes, which may be the same or different.

Therapeutic Applications

Another aspect of the invention relates to a conjugate as described above for use in medicine.

Yet another aspect relates to the use of a conjugate of the invention in the preparation of a medicament for treating an immune disorder.

In one preferred embodiment, the immune disorder is an autoimmune disease.

In one particularly preferred embodiment, the disorder is multiple sclerosis (MS).

MS is a serious autoimmune disease in which the destruction of myelin sheath and loss of neurologic function takes place [Steinman, 1996]. The linear peptides $MBP_{83-99}$: H-Glu-Asn-Pro-Val-Val-His-Phe-Phe-Lys-Asn-Ile-Val-Thr-Pro-Arg-Thr-Pro-OH (SEQ ID NO. 9), $PLP_{139-151}$: H-His-Ser-Leu-Gly-Lys-Trp-Leu-Gly-His-Pro-Asp-Lys-Phe-OH (SEQ ID NO. 10) and $MOG_{35-55}$: H-Met-Glu-Val-Gly-Trp-Tyr-Arg-Pro[Ser]-Pro-Phe-Ser-Arg-Val-Val-His-Leu-Tyr-Arg-Asn-Gly-Lys-OH (SEQ ID NO. 11) were found to induce EAE in animal models. However, their conjugation to reduced or oxidized mannan completely prevented the induction of EAE.

In another preferred embodiment, the disorder is experimental autoimmune encephalomyelitis (EAE).

In one preferred embodiment, the EAE is $MBP_{74-85}$-induced EAE.

In one preferred embodiment, the EAE is $MBP_{83-89}$-induced EAE.

In another preferred embodiment, the EAE is $MOG_{35-55}$-induced EAE.

In yet another preferred embodiment, the EAE is $PLP_{131-139}$-induced EAE.

A further aspect of the invention relates to a method of treating an immune disorder, said method comprising administering to a subject a conjugate as defined above.

Preferably, the immune disorder is an autoimmune disease. More preferably, the disorder is multiple sclerosis (MS) or experimental autoimmune encephalomyelitis (EAE).

Yet another aspect of the invention relates to a method of immunizing a subject against an immune disorder, said method comprising administering to a subject a conjugate as defined above.

Preferably, the peptide or conjugate is administered in an amount sufficient to cause suppression of chronic experimental autoimmune encephalomyelitis (EAE).

Another aspect of the invention relates to a conjugate or mixture according the invention for the treatment of an immune disorder.

Pharmaceutical Composition

Another aspect relates to a pharmaceutical composition comprising a peptide or a conjugate according to the invention, admixed with a pharmaceutically acceptable diluent, excipient or carrier.

Even though the conjugates of the present invention (including their pharmaceutically acceptable salts, esters and pharmaceutically acceptable solvates) can be administered alone, they will generally be administered in admixture with a pharmaceutical carrier, excipient or diluent, particularly for human therapy. The pharmaceutical compositions may be for human or animal usage in human and veterinary medicine.

Examples of such suitable excipients for the various different forms of pharmaceutical compositions described herein may be found in the "Handbook of Pharmaceutical Excipients, $2^{nd}$ Edition, (1994), Edited by A Wade and P J Weller.

Acceptable carriers or diluents for therapeutic use are well known in the pharmaceutical art, and are described, for example, in Remington's Pharmaceutical Sciences, Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

Vaccines

Another aspect of the invention relates to a vaccine or immunogenic composition comprising a conjugate as defined above.

The immunogenic compositions of the invention are preferably adjuvanted. Adjuvants used in the present invention are those which are physiologically acceptable to humans, these include, but are not limited to an aluminium salt such as aluminium hydroxide gel (alum) or aluminium phosphate, but may also be a salt of calcium, iron or zinc, oil/surfactant based emulsion adjuvants such as Montanide™ in which different surfactants (especially mannityl oleate) are combined with a mineral oil, squalene-containing emulsions such as MF59™, monophosphoryl lipid A, or Neisseriae mutant lipopolysaccharide, an insoluble suspension of acylated tyrosine, or acylated sugars, cationically or anionically derivatised polysaccharides, or polyphosphazenes.

Preferably the adjuvant is administered at the same time as of the invention and in preferred embodiments are formulated together.

The vaccine composition of the present invention preferably is sterile. Furthermore, the composition may contain components that preserve against infestation with, and growth of, micro-organisms.

It is preferred that the vaccine composition is manufactured in the form of a sterile aqueous liquid which is ready for immediate administration.

In a preferred embodiment of the invention, the inventive vaccine composition may be formulated in dosage unit form as heretofore described to facilitate administration and ensure uniformity of dosage. Formulation may be effected using available techniques, such as those applicable to preparations of emulsions.

Salts/Esters

The peptides/conjugates of the invention can be present as salts or esters, in particular pharmaceutically acceptable salts or esters.

Pharmaceutically acceptable salts of the peptides/conjugates of the invention include suitable acid addition or base salts thereof. A review of suitable pharmaceutical salts may be found in Berge et al, J Pharm Sci, 66, 1-19 (1977). Salts are formed, for example with strong inorganic acids such as mineral acids, e.g. sulphuric acid, phosphoric acid or hydrohalic acids; with strong organic carboxylic acids, such as alkanecarboxylic acids of 1 to 4 carbon atoms which are unsubstituted or substituted (e.g., by halogen), such as acetic acid; with saturated or unsaturated dicarboxylic acids, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_1\text{-}C_4)$-alkyl- or aryl-sulfonic acids which are unsubstituted or substituted (for example, by a halogen) such as methane- or p-toluene sulfonic acid.

Esters are formed either using organic acids or alcohols/hydroxides, depending on the functional group being esterified. Organic acids include carboxylic acids, such as alkanecarboxylic acids of 1 to 12 carbon atoms which are unsubstituted or substituted (e.g., by halogen), such as acetic acid; with saturated or unsaturated dicarboxylic acid, for example oxalic, malonic, succinic, maleic, fumaric, phthalic or tetraphthalic; with hydroxycarboxylic acids, for example ascorbic, glycolic, lactic, malic, tartaric or citric acid; with aminoacids, for example aspartic or glutamic acid; with benzoic acid; or with organic sulfonic acids, such as $(C_1\text{-}C_4)$-alkyl- or aryl-sulfonic acids which are unsubstituted or substituted (for example, by a halogen) such as methane- or p-toluene sulfonic acid. Suitable hydroxides include inorganic hydroxides, such as sodium hydroxide, potassium hydroxide, calcium hydroxide, aluminium hydroxide. Alcohols include alkanealcohols of 1-12 carbon atoms which may be unsubstituted or substituted, e.g. by a halogen).

Enantiomers/Tautomers

In all aspects of the present invention previously discussed, the invention includes, where appropriate all enantiomers and tautomers of the peptides/conjugates. The man skilled in the art will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Some of the peptides/conjugates of the invention may exist as stereoisomers and/or geometric isomers—e.g. they may possess one or more asymmetric and/or geometric centres and so may exist in two or more stereoisomeric and/or geometric forms. The present invention contemplates the use of all the individual stereoisomers and geometric isomers, and mixtures thereof. The terms used in the claims encompass these forms, provided said forms retain the appropriate functional activity (though not necessarily to the same degree).

The present invention also includes all suitable isotopic variations of the peptides/conjugates or pharmaceutically acceptable salts thereof. An isotopic variation is defined as one in which at least one atom is replaced by an atom having the same atomic number but an atomic mass different from the atomic mass usually found in nature. Examples of isotopes that can be incorporated into the peptides/conjugates and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$, and $^{36}Cl$, respectively. Certain isotopic variations of the peptides/conjugates and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the peptides/conjugates of the present invention and pharmaceutically acceptable salts thereof of this invention can generally be prepared by conventional procedures using appropriate isotopic variations of suitable reagents.

Solvates

The present invention also includes the use of solvate forms of the peptides/conjugates of the present invention. The terms used in the claims encompass these forms.

Polymorphs

The invention furthermore relates to the peptides/conjugates of the present invention in their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

The invention further includes the peptides/conjugates of the present invention in prodrug form. Such prodrugs are generally peptides/conjugates wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Administration

The pharmaceutical compositions of the present invention may be adapted for oral, rectal, vaginal, parenteral, intramuscular, intraperitoneal, intraarterial, intrathecal, intrabronchial, subcutaneous, intradermal, intravenous, nasal, buccal or sublingual routes of administration.

For oral administration, particular use is made of compressed tablets, pills, tablets, gellules, drops, and capsules.

Other forms of administration comprise solutions or emulsions which may be injected intravenously, intraarterially, intrathecally, subcutaneously, intradermally, intraperitoneally or intramuscularly, and which are prepared from sterile or sterilisable solutions. The pharmaceutical compositions of the present invention may also be in form of suppositories, pessaries, suspensions, emulsions, lotions, ointments, creams, gels, sprays, solutions or dusting powders.

An alternative means of transdermal administration is by use of a skin patch. For example, the active ingredient can be incorporated into a cream consisting of an aqueous emulsion of polyethylene glycols or liquid paraffin. The active ingredient can also be incorporated, at a concentration of between 1 and 10% by weight, into an ointment consisting of a white wax or white soft paraffin base together with such stabilisers and preservatives as may be required.

Compositions may be formulated in unit dosage form, i.e., in the form of discrete portions containing a unit dose, or a multiple or sub-unit of a unit dose.

Dosage

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Combinations

In a particularly preferred embodiment, one or more peptides/conjugates of the invention are administered in combination with one or more other therapeutically active agents, for example, existing drugs available on the market. In such cases, the compounds of the invention may be administered consecutively, simultaneously or sequentially with the one or more other agents.

Combination therapy is desirable in order to avoid an overlap of major toxicities, mechanism of action and resistance mechanism(s). Furthermore, it is also desirable to administer most drugs at their maximum tolerated doses with minimum time intervals between such doses. The major advantages of combining chemotherapeutic drugs are that it may promote additive or possible synergistic effects through biochemical interactions and also may decrease the emergence of resistance in early tumor cells which would have been otherwise responsive to initial chemotherapy with a single agent.

Assay

A further aspect of the invention relates to a conjugate as defined above in an assay for elucidating agents capable of regulating experimental autoimmune encephalomyelitis (EAE) or regulating multiple sclerosis.

The present invention is further described by way of the following non-limiting examples, and with reference to the following figures wherein.

FIG. 6 shows the results for individual mice of each of the experimental groups for which histological analysis was performed following MOG$_{35-55}$-EAE induction. Spinal cord infiltration and demyelination in addition to brain infiltration and demyelination are shown. (Abbreviations: ubi=ubiquitous, cer=cerebellum, men=meninges, vac=vacuolation). Inflammation in the spinal cord was determined by absolute true quantification; the numbers mean inflammatory infiltrates/mm$^2$ of tissue. In the brain a semi-quantitative scoring was used according to which 0.5=single perivascular infiltrates; 1=multiple inflammatory infiltrates. Demyelination was scored as follows: 0.5: single perivascular sleeves of demyelination, 1: ubiquitous perivascular or subpial demyelination, 2: confluent demyelinated plaques, 3: profound focal demyelination, involving about ½ of the spinal cord white matter at least in one spinal cord segment, 4: extensive demyelination, for instance complete demyelination of spinal cord white matter at least in one segment of the spinal cord. Controls 1, 2, 3 are the same as PBS-control, because the experiment was carried out twice.

Figure 7:
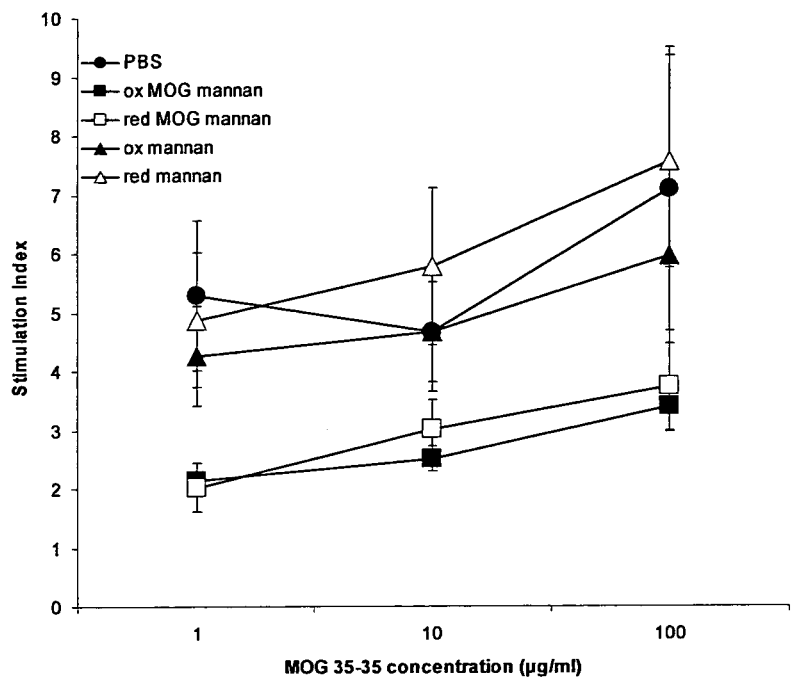

FIG. 7 shows the proliferation of splenocytes isolated 25 days post-MOG$_{35-55}$-EAE induction from mice immunized with oxidized/reduced mannan-MOG$_{35-55}$, oxidized/reduced mannan alone, or PBS as control. Splenocytes were ex vivo stimulated with increasing concentrations of MOG$_{35-55}$ peptide. (PBS control, closed circles, n=4; oxidized mannan MOG$_{35-55}$, closed squares, n=6; reduced mannan MOG$_{35-55}$, open squares, n=6; oxidized mannan, closed triangles, n=5; reduced mannan, open triangles, n=4).

Figure 8:
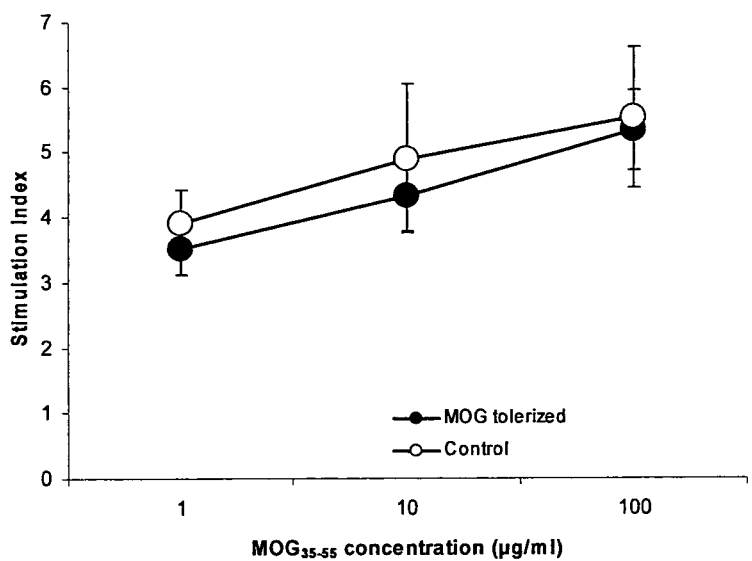

FIG. 8 shows the proliferation of splenocytes isolated 25 days post-MOG$_{35-55}$-EAE induction from mice that were immunized with MOG$_{35-55}$ peptide alone, and stimulated ex vivo with increasing concentrations of MOG$_{35-55}$ peptide. (PBS control, open circles, n=3; MOG$_{35-55}$ peptide, closed circles, n=6).

Figure 9:
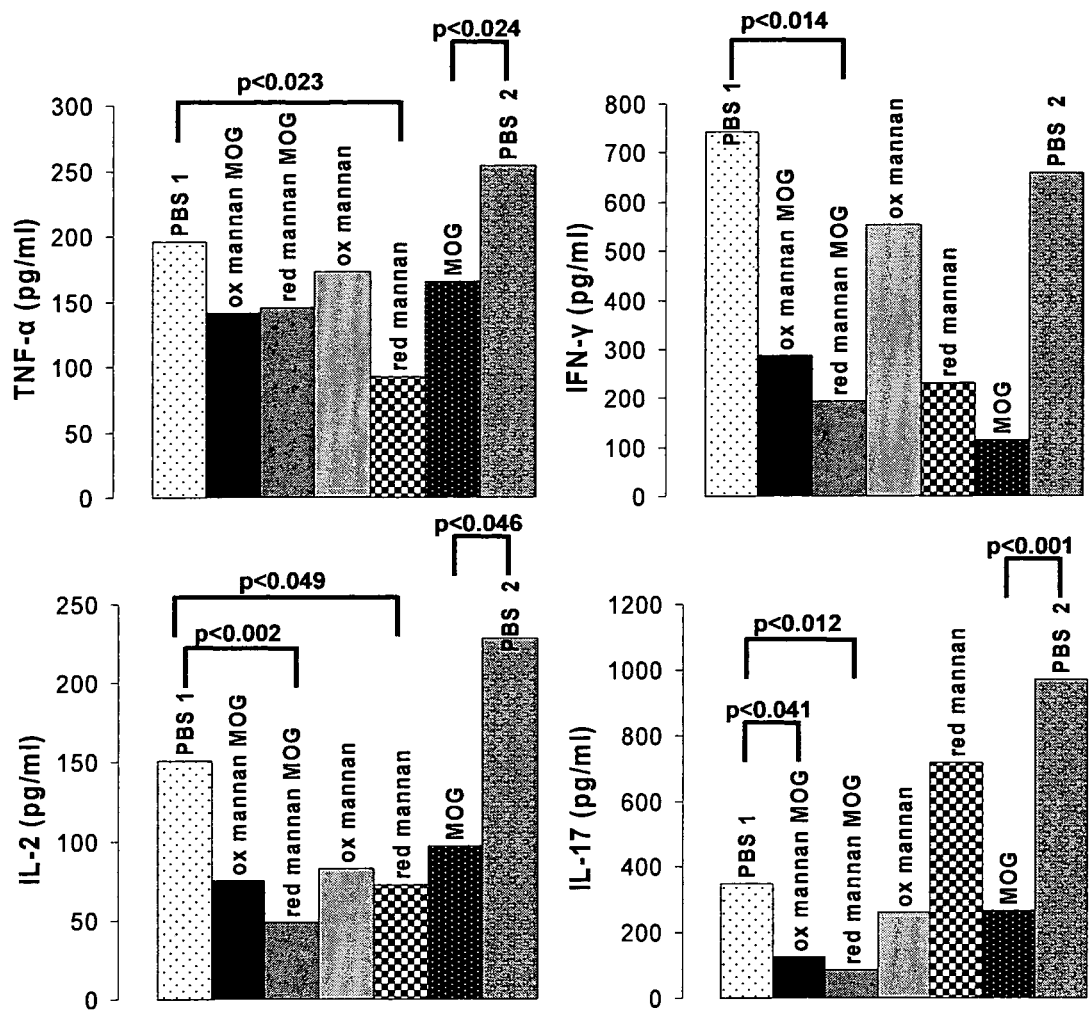

FIG. 9 shows cytokine production measured in culture supernatants of splenocytes that were stimulated for 48 hours with 10 μg/ml MOG$_{35-55}$ peptide. Splenocytes were isolated 25 days post MOG$_{35-55}$-EAE induction. Statistical significance after pair-wise comparisons (using T-Test and Mann Whitney rank sum test) of each experimental group with the non-vaccinated control (PBS) group is shown. PBS1, PBS2 are controls.

Figure 10:
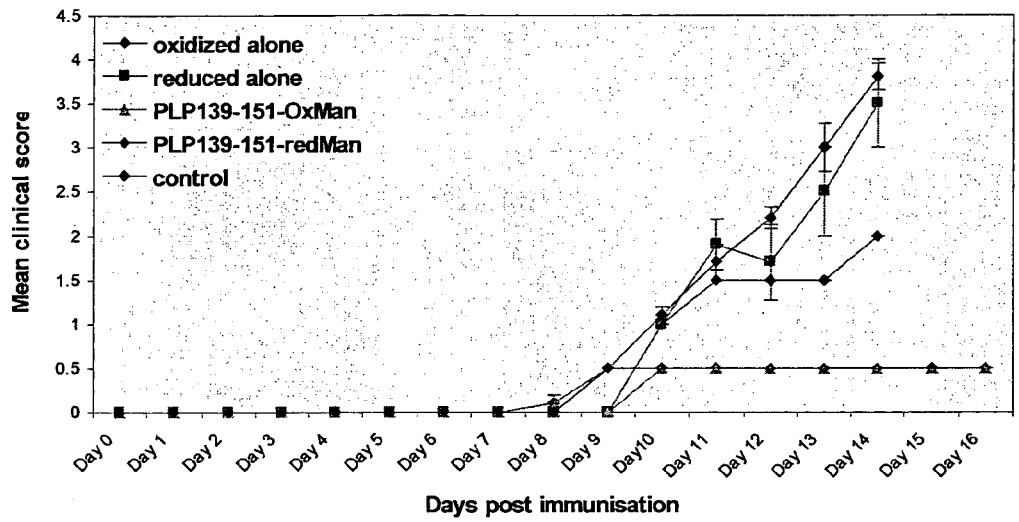

FIG. 10 shows the mean clinical score of groups of mice which received prophylactic vaccination with oxidized/reduced mannan-PLP$_{139-151}$ peptide conjugates prior to PLP$_{139-151}$-EAE induction; control mice were non immunized (n=5 for all groups). Mice immunized with oxidized mannan alone, reduced mannan alone, or control mice were culled on day 14 for ethical reasons. The vaccinated group with PLP$_{139-151}$-oxidized mannan has the same clinical score as the control. It is completely protected.

Figure 11:
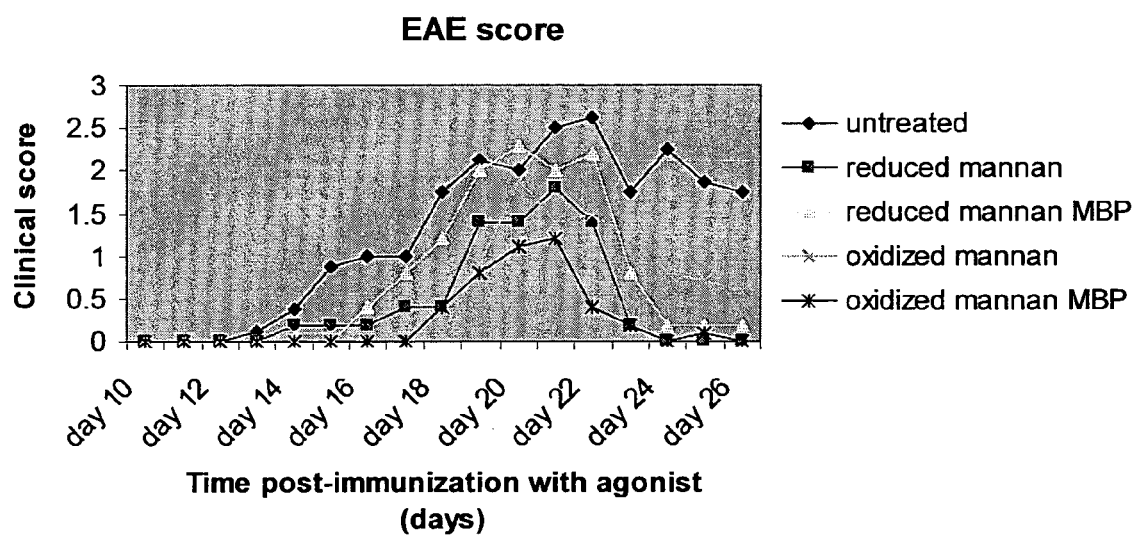

FIG. 11 shows the average clinical score Lewis rats that had received oxidized/reduced mannan-MBP$_{83-99}$ or oxidized/reduced mannan alone injections, prior to MBP$_{74-85}$ EAE induction. Naïve mice (non immunized) were used as controls (n=5 for all groups).

Figure 12:
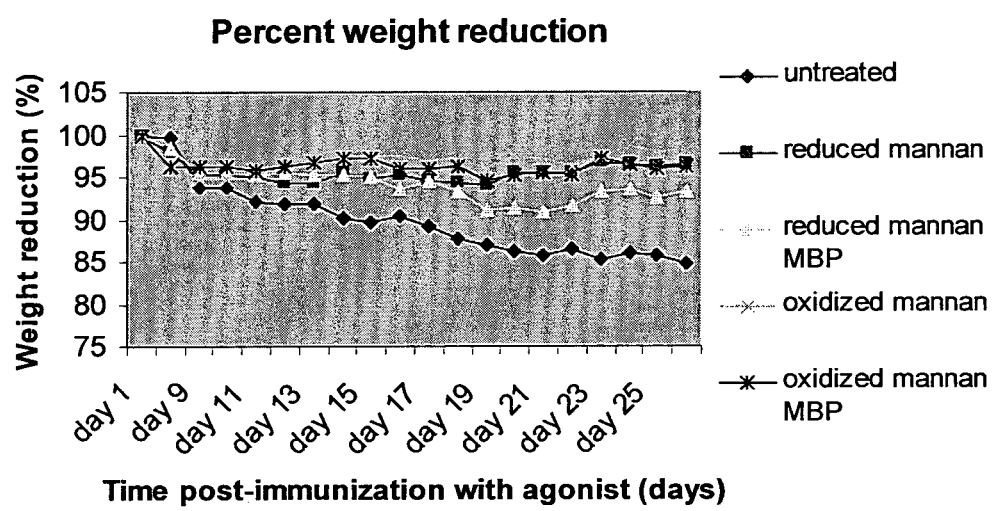

FIG. 12 shows the mean body weight changes in Lewis rats that were immunized with oxidized/reduced mannan-MBP$_{83-99}$ or oxidized/reduced mannan alone, or non immunized (controls), after MBP$_{74-85}$ EAE induction (n=5 for all groups).

EXAMPLES

Synthesis and Purification of Linear Myelin Epitopes: MBP$_{83-99}$, PLP$_{139-151}$ and MOG$_{35-55}$ with a [(Lys-Gly)$_5$] Bridge General Procedure In general, peptides were synthesized by Fmoc/tBu methodology using 2-chlorotrityl chloride (CLTR-C1) resin (0.7 mmol Cl$^-$/g) and N$^\alpha$—Fmoc (9-fluorenylmethyloxycarboxyl)-protected amino acids [Tselios et al., 1999; Tselios et al., 2000a; Tselios et al., 2000b; Tselios et al., 2002; Matsoukas et al., 2005; Mantzourani et al., 2006a; Mantzourani et al., 2006b; Mantzourani et al., 2007]. In particular, the linear protected peptides: MBP$_{83-99}$: H-Lys(Boc)-Gly-Lys(Boc)-Gly-Lys(Boc)-Gly-Lys(Boc)-Gly-Lys(Boc)-Gly-Glu(tBu)-Asn(Trt)-Pro-Val-Val-His(Trt)-Phe-Phe-Lys(Boc)-Asn(Trt)-Ile-Val-Thr(tBu)-Pro-Arg(Pdf)-Thr(tBu)-Pro-OH (SEQ ID NO. 9), PLP$_{139-151}$: H-Lys(Boc)-Gly-Lys(Boc)-Gly-Lys(Boc)-Gly-Lys(Boc)-Gly-Lys(Boc)-Gly-His(Trt)-Ser(tBu)-Leu-Gly-Lys(Boc)-Trp-Leu-Gly-His(Trt)-Pro-Asp-Lys(Boc)-Phe-OH (SEQ ID NO. 10) and MOG$_{35-55}$: H-Lys(Boc)-Gly-Lys(Boc)-Gly-Lys(Boc)-Gly-Lys(Boc)-Gly-Lys(Boc)-Gly-Met-Glu(tBu)-Val-Gly-Trp-Tyr(tBu)-Arg(Pbf)-Pro(Ser)-Pro-Phe-Ser(tBu)-Arg(Pbf)-Val-Val-His(Trt)-Leu-Tyr(tBu)-Arg(Pbf)-Asn(Trt)-Gly-Lys(Boc)-OH (SEQ ID NO. 11) were synthesized step by step on the solid polymer (CLTR-C1) using N,N'-diisopropyl-carbodiimide and 1-hydroxybenzotriazol as coupling reagent in DMF. The Kaiser test and thin layer chromatography (TLC) in n-butanol/acetic acid/water (4:1:1) (BAW) as elutant verified the completeness of each coupling. The protected, on the resin, peptides were treated with the splitting mixture DCM/HFIP (7/3) for 6 h at room temperature to remove peptide from the resin. The mixture was filtered off and the resin was washed twice with the splitting mixture and with DCM. The solvent was removed on a rotary evaporator and the obtained oily product was precipitated from cold and dry diethyl ether as a white solid. The protected linear peptides were treated with the deprotection mixture DCM/TFA/ethanedithiol/anisole (32/65/2/1) for 6 h at room temperature. The resulting solution was concentrated under vacuum to a small volume (0.5 ml). The final crude products were further purified using semi-preparative Reverse Phase-High Performance Liquid Chromatography (RP-HPLC). The purity of peptides was determined using RP-HPLC, and the identification was achieved by ESI-MS and Amino Acid analysis.

Solid-Phase Peptide Synthesis of Linear and Cyclic Analogues

Peptides (Table 1) were prepared on 2-chlorotrityl chloride resin (CTLR-C1) using Fmoc/tBu methodology. The cyclization was achieved with TBTU/HOAt and 2,4,6-collidine as base, as previously described. Preparative HPLC for peptide analogues were performed using a Lichrosorb RP-18 reversed phase semipreparative column with 7 nm packing material. The peptides were >95% pure as analysed by mass spectrometry.

of the cyclo(91-99)[Ala$^{96}$] MBP$_{83-99}$. Each one of the linear protected peptide was dissolved in DMF and collidine/HOAt was added. This mixture was added dropwise in a solution of TBTU in DMF for 8 hours. The cyclization was determined by TLC and analytical reversed phase HPLC (RP-HPLC). The solvent was removed under reduced pressure affording a light yellow oily residue. The cyclic protected peptide (purity ≥90%) was precipitated from H$_2$O and dried in vacuum for 16 h. The cyclic protected peptide was treated with 65% TFA in DCM and 3% ethanodithiol as scavenger for 4 hours at room temperature. The resulting solution was concentrated to a small volume and the final free peptide was precipitated as a light yellow amorphous solid added diethylether (purity ≥80%). Peptide purity was assessed by analytical HPLC reruns, thin layer chromatography (TLC) and mass spectrometry (ESIMS).

TABLE 1

MBP$_{83-99}$ peptide analogues used in this study

| | Sequence | Peptide analogues |
|---|---|---|
| P1(SEQ ID NO. 1) | E N P V V H F F K N I V T P R T P | MBP$_{83-99}$ |
| P2(SEQ ID NO. 1) | cyclo(83-99)E N P V V H F F K N I V T P R T Р | cyclo(83-99)MBP$_{83-99}$ |
| P3(SEQ ID NO. 18) | E N P V V H F F <u>A</u> N I V T P R T P | [A$^{91}$]MBP$_{83-99}$ |
| P4(SEQ ID NO. 18) | cyclo(83-99)E N P V V H F F <u>A</u> N I V T P R T Р | cyclo(83-99)[A$^{91}$]MBP$_{83-99}$ |
| P5(SEQ ID NO. 15) | E N P V V H F F <u>E</u> N I V T P R T P | [E$^{91}$]MBP$_{83-99}$ |
| P6(SEQ ID NO. 16) | E N P V V H F F <u>F</u> N I V T P R T P | [F$^{91}$]MBP$_{83-99}$ |
| P7(SEQ ID NO. 12) | E N P V V H F F <u>R</u> N I V T <u>A</u> R T P | [R$^{91}$, A$^{96}$]MBP$_{83-99}$ |
| P8(SEQ ID NO. 17) | E N P V V H F F <u>Y</u> N I V T P R T P | [Y$^{91}$]MBP$_{83-99}$ |
| P9(SEQ ID NO. 13) | E N P V V H F F <u>A</u> N I V T <u>A</u> R T P | [A$^{91}$, A$^{96}$]MBP$_{83-99}$ |

Examples of Cyclization

Cyclization of linear MBP$_{83-99}$ protected analogue was achieved using O-benzotriazol-1-yl-N,N,N',N'-tetramethyluronium tetrafluoroborate (TBTU) and 1-hydroxy-7-azabenzotriazole, 2,4,6 collidine in DMF solution, allowing fast reactions and high yield cyclization products. Recent results indicate that HOAt, a 4-nitrogen containing variant, is a very effective coupling additive, more efficient than HOBt for solution or solid phase synthesis leading in high yield products.

Synthesis of Human MBP Cyclic Peptides

```
Synthesis of human MBP cyclic peptides
                                         (SEQ ID NO. 12)
Cyclo(83-99)[Arg⁹¹, Ala⁹⁶] MBP₈₃₋₉₉ (Glu-Asn-Pro-
Val-Val⁸⁷-His-Phe-Phe-Arg⁹¹-Asn-Ile-Val-Thr-Ala⁹⁶-
Arg-Thr-Pro⁹⁹)

(SEQ ID NO. 25)
Cyclo(91-99)[Ala⁹⁶] MBP₈₃₋₉₉ (Glu-Asn-Pro-Val-
Val⁸⁷-His-Phe-Phe-Lys⁹¹-Asn-Ile-Val-Thr-Ala⁹⁶-Arg-
Thr-Pro⁹⁹)
```

Human MBP cyclic analogues were prepared on 2-chlorotrityl chloride resin using Fmoc/tBu methodology. The peptide synthesis was achieved using DIC/HOBt in DMF and the N$^\alpha$-NH$_2$ of amino acids was protected with the Fmoc group. The side chain of peptides was protected as following: Trt for His, Pbf for Arg, tBu for Ser, Thr, Asp, Glu, Boc for Lys, as regarding the cyclic analogue cyclo(91-99)[Ala$^{96}$] MBP$_{83-99}$ (by Nε-NH$_2$ of Lys and C-terminous) Mtt protected group was used, because it can easily be removed using mixture HFIP(1,1,1,3,3,3 hexafluoro-2-propanol)/DCM (2/8), which cleaves peptides from the resin. Otherwise, the side chain of Lys of the cyclo(87-99)[Arg$^{91}$, Ala$^9$]MBP$_{87-99}$ was protected with Boc group. The final protected linear peptides on resin were dried in vacuum and then treated with the splitting mixture DCM/HFIP (8/2) for 7 h at room temperature to release the peptide from the resin and deprotect Lys from Mtt Solid-Phase Peptide Synthesis of Linear Analogs Peptides MBP$_{87-99}$ (VHFFKNIVTPRTP; SEQ ID NO. 23), [R$^{91}$, A$^9$]MBP$_{87-99}$ (VHFF<u>R</u>NIVT<u>A</u>RTP; SEQ ID NO. 26) and [A$^{91}$, A$^9$]MBP$_{87-99}$ (VHFF<u>A</u>NIVT<u>A</u>RTP; SEQ ID NO. 24) were prepared on 2-chlorotrityl chloride resin (CLTR-C1) using Fmoc/tBu methodology[22, 48-51]. Preparative HPLC for MBP$_{87-99}$, [R$^{91}$, A$^9$]MBP$_{87-99}$ and [A$^{91}$, A$^9$]MBP$_{87-99}$ peptide analogs were performed using a Lichrosorb RP-18 reversed phase semipreparative column with 7 μm packing material. The peptides were >95% pure as analyzed by analytical RP-HPLC and ESI-MS.

References for Solid-Phase Peptide Synthesis of Linear Analogs

22. Matsoukas, J.; Apostolopoulos, V.; Kalbacher, H.; Papini, A. M.; Tselios, T.; Chatzantoni, K.; Biagioli, T.; Lolli, F.; Deraos, S.; Papathanassopoulos, P.; Troganis, A.; Mantzourani, E.; Mavromoustakos, T.; Mouzaki, A. Design and synthesis of a novel potent myelin basic protein epitope 87-99 cyclic analogue: enhanced stability and biological properties of mimics render them a potentially new class of immunomodulators. *J Med Chem* 2005, 48, 1470-80.

48. Tselios, T.; Apostolopoulos, V.; Daliani, I.; Deraos, S.; Grdadolnik, S; Mavromoustakos, T.; Melachrinou, M.; Thymianou, S.; Probert, L.; Mouzaki, A.; Matsoukas, J.

Antagonistic effects of human cyclic MBP(87-99) altered peptide ligands in experimental allergic encephalomyelitis and human T-cell proliferation. *J Med Chem* 2002, 45, 275-83.

49. Tselios, T.; Daliani, I.; Deraos, S.; Thymianou, S.; Matsoukas, E.; Troganis, A.; Gerothanassis, I.; Mouzaki, A.; Mavromoustakos, T.; Probert, L.; Matsoukas, J. Treatment of experimental allergic encephalomyelitis (EAE) by a rationally designed cyclic analogue of myelin basic protein (MBP) epitope 72-85. *Bioorg Med Chem Lett* 2000, 10, 2713-7.

50. Tselios, T.; Daliani, I.; Probert, L.; Deraos, S.; Matsoukas, E.; Roy, S.; Pires, J.; Moore, G.; Matsoukas, J. Treatment of experimental allergic encephalomyelitis (EAE) induced by guinea pig myelin basic protein epitope 72-85 with a human MBP(87-99) analogue and effects of cyclic peptides. *Bioorg Med Chem* 2000, 8, 1903-9.

51. Tselios, T.; Probert, L.; Daliani, I.; Matsoukas, E.; Troganis, A.; Gerothanassis, I. P.; Mavromoustakos, T.; Moore, G. J.; Matsoukas, J. M. Design and synthesis of a potent cyclic analogue of the myelin basic protein epitope MBP72-85: importance of the Ala81 carboxyl group and of a cyclic conformation for induction of experimental allergic encephalomyelitis. *J Med Chem* 1999, 42, 1170-7.

Solid-Phase Peptide Synthesis of Cyclic Analogs

Peptides $MBP_{87-99}$ (VHFFKNIVTPRTP; SEQ ID NO. 23) and cyclic double mutant peptide with Ala mutations at positions 91 and 96, cyclo(87-99)[$A^{91}$, $A^{96}$]$MBP_{87-99}$ (cyclo, head-to-tail, VHFF$\underline{A}$NIVT$\underline{A}$RTP; SEQ ID NO. 24) were prepared on 2-chlorotrityl chloride resin (CLTR-C1) using Fmoc/tBu methodology. Head-to-tail cyclization of $MBP_{87-99}$[$A^{91}$, $A^{96}$] peptide was achieved using O-benzotriazol-1-yl-N,N,N',N'-tetramethyluronium tetrafluoroborate (TBTU) and 1-hydroxy-7-azabenzotriazole, 2,4,6 collidine in DMF solution, allowing fast reactions and high yield cyclization products. Results indicate that HOAt, a 4-nitrogen containing variant, is a very effective coupling additive, more efficient than HOBt for solution or solid phase synthesis[14-17]. Preparative HPLC for peptide analogs were performed using a Lichrosorb RP-18 reversed phase semi-preparative column with 7 μm packing material. The peptides were >95% pure as analyzed by mass spectrometry (ESI-MS).

References for Solid-Phase Peptide Synthesis of Cyclic Analogs

14. Tselios, T.; Apostolopoulos, V.; Daliani, I.; Deraos, S.; Grdadolnik, S.; Mavromoustakos, T.; Melachrinou, M.; Thymianou, S.; Probert, L.; Mouzaki, A.; Matsoukas, J. Antagonistic effects of human cyclic MBP(87-99) altered peptide ligands in experimental allergic encephalomyelitis and human T-cell proliferation. *J Med Chem* 2002, 45, 275-83.

15. Tselios, T.; Daliani, I.; Deraos, S.; Thymianou, S.; Matsoukas, E.; Troganis, A.; Gerothanassis, I.; Mouzaki, A.; Mavromoustakos, T.; Probert, L.; Matsoukas, J. Treatment of experimental allergic encephalomyelitis (EAE) by a rationally designed cyclic analogue of myelin basic protein (MBP) epitope 72-85. *Bioorg Med Chem Lett* 2000, 10, 2713-7.

16. Tselios, T.; Daliani, I.; Probert, L.; Deraos, S.; Matsoukas, E.; Roy, S.; Pires, J.; Moore, G.; Matsoukas, J. Treatment of experimental allergic encephalomyelitis (EAE) induced by guinea pig myelin basic protein epitope 72-85 with a human MBP(87-99) analogue and effects of cyclic peptides. *Bioorg Med Chem* 2000, 8, 1903-9.

17. Tselios, T.; Probert, L.; Daliani, I.; Matsoukas, E.; Troganis, A.; Gerothanassis, I. P.; Mavromoustakos, T.; Moore, G. J.; Matsoukas, J. M. Design and synthesis of a potent cyclic analogue of the myelin basic protein epitope MBP72-85: importance of the Ala81 carboxyl group and of a cyclic conformation for induction of experimental allergic encephalomyelitis. *J Med Chem* 1999, 42, 1170-7.

Conjugation of Peptides to Mannan

The peptide-mannan binding was achieved following a protocol earlier described [Apostolopoulos et al., 1996; Tselios et al., 2005]. Briefly, 14 mg mannan (poly-mannose from *Saccharomyces cerevisiae*, Sigma-Aldrich Ltd, Athens, Greece) was dissolved in 1 ml phosphate buffer, pH 6.0, and oxidized to polyaldehyde by treating with sodium periodate. The mixture was passed through a PD-10 column (Sephadex G-25 M column, Pharmacia Biotech. Sweden) equilibrated with 0.1 M bicarbonate buffer pH 9.0 and the mannan fraction collected. Oxidized mannan (7.0 mg/ml) was eluted with 2 ml of pH 9.0 phosphate buffer, to which 1 mg peptides containing [(Lys-Gly)$_5$] bridge were added and allowed to react overnight at room temperature in the dark. Conjugation occurs via Schiff base formation between free amino groups of Lys and oxidized mannan. Reduced mannan-peptide complexes were prepared by adding 1 mg sodium borohydride to each mixture for 6-8 h at room temperature in the dark. The cyclic peptide-mannan binding was achieved through a Lys residue following same protocol as above.

Mannan Conjugated Peptide Vaccinations

Groups of female animals (age range 6-10 week old C57BL/6 or SJL/J mice and 12-15 week old Lewis rats) were immunized intra-dermally with 100 μl solution containing 30 μg peptide ($MOG_{35-55}$) or 50 μg $PLP_{139-151}$ peptide for mice and 30 μg $MBP_{83-99}$ for Lewis rats) conjugated to 70 μg oxidized or reduced mannan diluted in bi-carbonate buffer, pH 9.0. As controls, age matched groups of animals were vaccinated with oxidized or reduced mannan alone, saline or 30-50 μg of peptide alone. Three consecutive vaccinations were performed spaced 15 days apart. Fifteen days after the last vaccination EAE was induced.

Induction-Inhibition and Assessment of $MOG_{35-55}$-EAE in C57BL/6 Mice

EAE was induced in C57BL/6 mice by subcutaneous (s.c) tail base injection of 50 μg of $MOG_{35-55}$ emulsified in Complete Freund's Adjuvant (CFA) supplemented with 400 μg of H37Ra *M. tuberculosis* (Difco). Mice also received an intra-peritoneal (i.p) injection of 200 ng of pertussis toxin (Sigma-Aldrich, Greece) on days 0 and 2. Mice were assessed daily for clinical signs according to the following scale: 0, normal; 1, limp tail; 2, hind limb weakness; 3, hind limb paralysis; 4, forelimb paralysis; and 5, moribund or death (0.5 gradations represent intermediate scores). Weights of mice were also monitored daily. Mice were allowed free access to food and water throughout the experiment.

Induction-Inhibition and Assessment of $PLP_{139-151}$-EAE in SJL/J Mice

EAE was induced in SJL/J mice using a standard protocol. 150 μg of $PLP_{139-151}$ was dissolved in PBS and emulsified in an equal volume of CFA (containing 1 μg/ml of heat killed *Mycobacterium Tuberculosis* HR37a, Sigma). On Day 0 (day of disease induction), one s.c injection was given by injecting 150 μg $PLP_{139-151}$/200 μl per mouse in both of the flanks. Each mouse also received 400 ng pertussis toxin (Sigma, P2980) (i.p) dissolved in 200 μl PBS. On day 2, mice were received a booster of pertussis toxin (200 ng pertussis toxin dissolved in 200 μl PBS per mouse) Animals were daily evaluated for clinical signs of disease, starting from day 1 post immunisation, using a 6-grade clinical scale: 0, normal animal; 0.5, weight loss; 1, inability to elevate the tail above the horizontal level, tail weakness; 2, tail paralysis; 3, tail paralysis/hind limb paresis; 4, hind limb paralysis/forelimb weakness; 5, quadriplegia/moribund; 6, death from EAE. Moreover, animals were daily weighted throughout the entire experimental period.

Induction and Assessment of $MBP_{74-85}$-EAE in Lewis Rats

EAE was induced in female Lewis rats by s.c. injection in hind foot pads of 30 μg $MPB_{74-85}$ peptide emulsified in CFA supplemented with 400 μg of H37Ra *M. tuberculosis* (Difco). Rats were assessed daily for clinical signs according to the following scale: 0, normal; 1, tail paralysis; 2, hind limb weakness; 3, hind limb paralysis; 4, forelimb paralysis; and 5, moribund or dead (0.5 gradations represent intermediate scores). Weights of the animals were also daily monitored. Rats were allowed free access to food and water throughout the experiment.

T Cell Priming and Proliferation Assays

Isolated splenocytes were cultured for 72 h in 96-well plates in RPMI 1640 (Invitrogen Life Technologies, Gaithersburg, Md.) containing 10% heat-inactivated FCS, 50 μM 2-ME, and increasing concentrations of $MOG_{35-55}$ peptide. Cells were stimulated in triplicate at $2 \times 10^6$ cells/ml in round-bottom, 96-well plates (Costar). Cells were pulsed with 1 μCi/$5 \times 10^5$ cells [$^3$H]-thymidine in triplicate (Amersham Radiochemicals) for the last 16 h of culture. [$^3$H]-thymidine incorporation was measured by liquid scintillation counting (Wallac, Turku, Finland). Results are expressed as the stimulation index (ratio between radioactivity counts of cells cultured in presence of peptide and cells cultured with media alone).

Measurement of Cytokines

The mouse Th1/Th2 cytokine cytometric bead array kit (BD Biosciences) was used to measure cytokine levels in culture supernatants according to the manufacturer's instructions. The cytokines measured with this kit were: IL-2, IL-4, IL-5, IFN-γ and TNF-α. In addition a mouse IL-17 ELISA set (R&D Systems, Germany) was used to measure cytokine secretion from splenocyte cell culture supernatants according to manufacturer's instructions. The sensitivity of the assay for different cytokines was as follows: IL-2, IL-4 and IL-5=5.0 pg/ml; IFN-γ=2.5 pg/ml; TNF-α=6.3 pg/ml.

Histopathological Analysis

Mice were transcardially perfused with ice-cold 4% paraformaldehyde in PBS under deep anesthesia. CNS tissues were postfixed in the same fixative for 3 h at 4° C. and processed for standard histopathological analysis. Inflammation was visualized by staining with H&E, whereas demyelination was demonstrated by a Luxol Fast Blue/periodic acid-chiff stain. Quantification of inflammation and demyelination was done in a blinded manner. Inflammation in the spinal cord was determined by absolute true quantification; the numbers mean inflammatory infiltrates/mm$^2$ of tissue. In the brain a semiquantitative scoring was used according to which 0.5 means single perivascular infiltrates; 1 means multiple inflammatory infiltrates. Demyelination was scored as follows: 0.5: single perivascular sleeves of demyelination, 1: ubiquitous perivascular or subpial demyelination, 2: confluent demyelinated plaques, 3: profound focal demyelination, involving about ½ of the spinal cord white matter at least in one spinal cord segment, 4: extensive demyelination, for instance complete demyelination of spinal cord white matter at least in one segment of the spinal cord.

Results and Discussion

Figure 1:
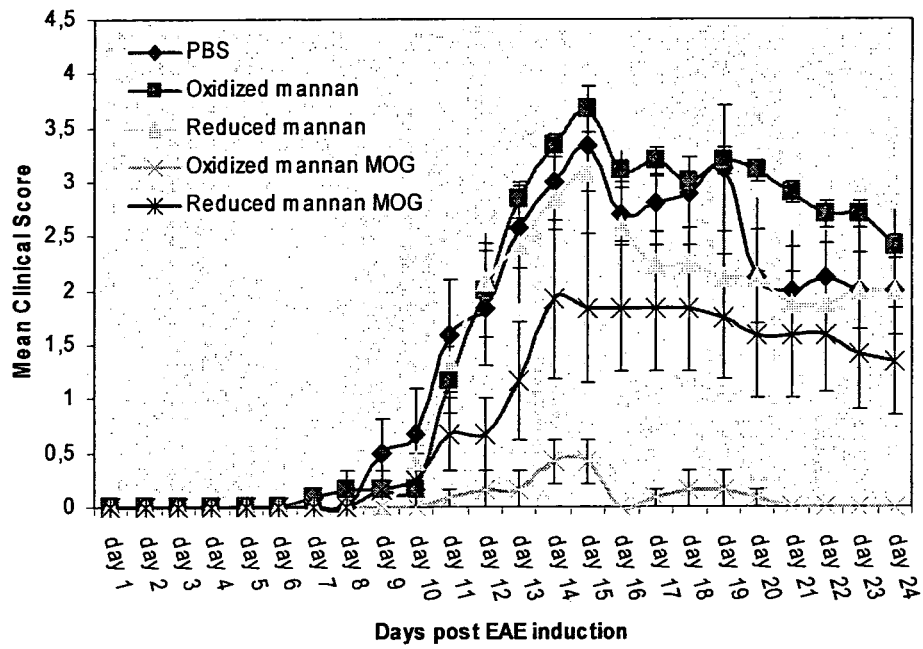
FIG. 1 shows the mean clinical score of groups of mice which received prophylactic vaccination with oxidized/reduced mannan-$MOG_{35-55}$ peptide conjugates prior to $MOG_{35-55}$-EAE induction (n=6 for all groups)
Figure 2:
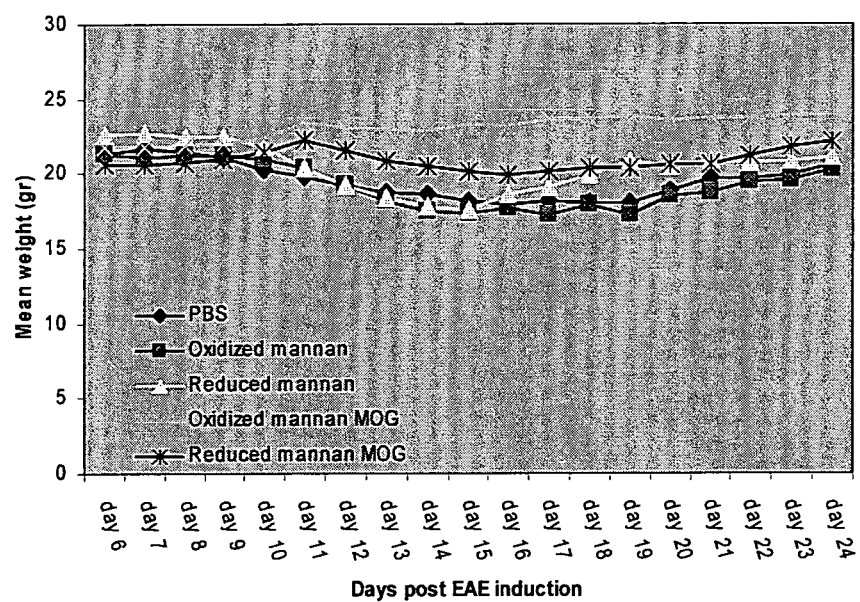
FIG. 2 shows the mean body weight changes in groups of mice that had received prophylactic vaccination with oxidized/reduced mannan-MOG$_{35-55}$ peptide conjugates prior to MOG$_{35-55}$-EAE induction.
Figure 3:
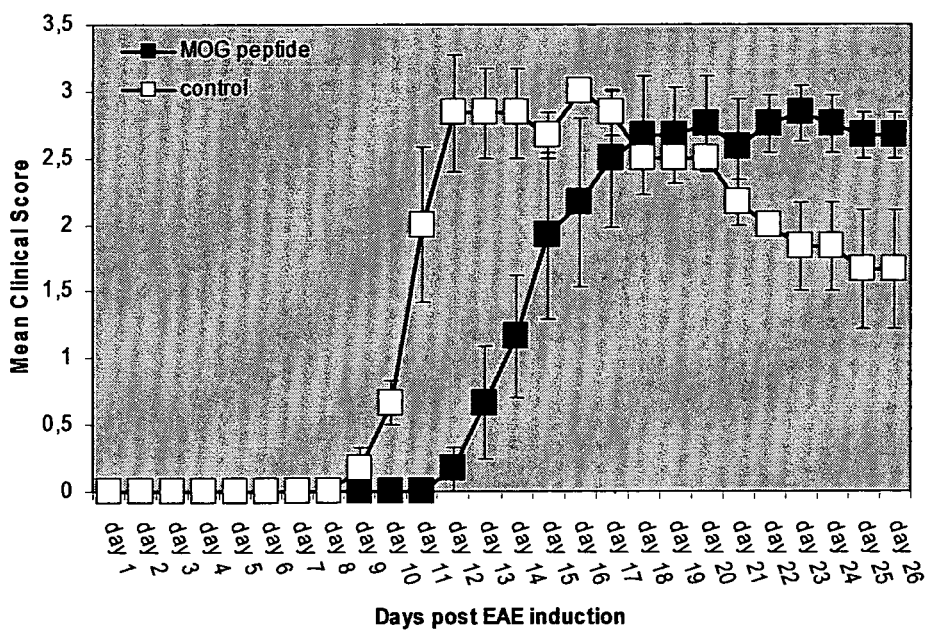
FIG. 3 shows the mean clinical scores of mice that received vaccination with MOG$_{35-55}$ peptide (black squares, n=6) prior to MOG$_{35-55}$-EAE induction. Non-vaccinated animals were used as controls (n=3, white squares).
Figure 4:
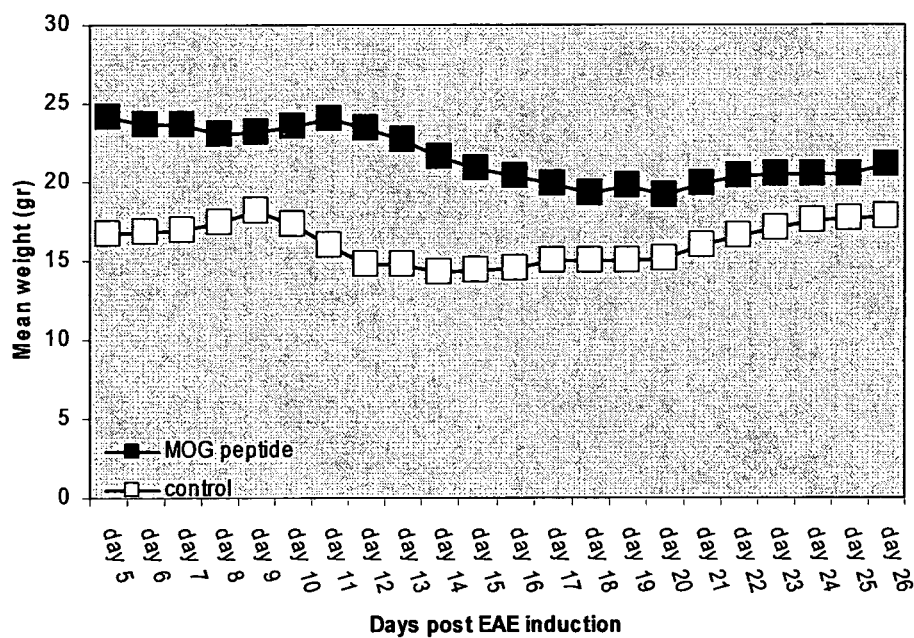
FIG. 4 shows the mean body weight changes in mice that received vaccination with MOG$_{35-55}$ peptide (black squares, n=6) prior to MOG$_{35-55}$-EAE induction. Non-vaccinated animals were used as controls (n=3, white squares).

Vaccination with Oxidized/Reduced Mannan-$MOG_{35-55}$ Peptide Conjugates Protect C57BL/6 Mice from $MOG_{35-55}$-EAE Triplicate vaccination of C57BL/6 mice with oxidized/reduced mannan-$MOG_{35-55}$ peptide conjugates allowed their significant protection from $MOG_{35-55}$-EAE development that was induced 15 days following the last vaccination (FIG. 1). $MOG_{35-55}$ peptide conjugated to oxidized mannan showed the greatest degree of protection as judged from the lowering of clinical score (FIG. 1) and the absence of wasting symptoms usually accompanying disease onset and progression as daily weight-measurement of experimental animals showed (FIG. 2). $MOG_{35-55}$ peptide conjugated to reduced mannan showed significant inhibition from disease manifestation as well. In order to exclude the possibility that there was an induction of tolerance to peptide due to repeated stimulation with it, we performed an equivalent experiment in which mice received triplicate vaccinations with unconjugated $MOG_{35-55}$ peptide spaced 15 days apart before $MOG_{35-55}$-EAE induction. Results showed that mice receiving three prior challenges with peptide alone were still susceptible to MOG-EAE and showed clinical signs of disease but characteristically: 1) EAE initiation was delayed in $MOG_{35-55}$ vaccinated animals by 3 days, 2) EAE was significantly lower in $MOG_{35-55}$ vaccinated animals compared to non vaccinated controls at initial stages of experimental disease and 3) disease was exacerbated in $MOG_{35-55}$ vaccinated animals after day 20 of disease progression (FIGS. 3 and 4).

Figure 5:
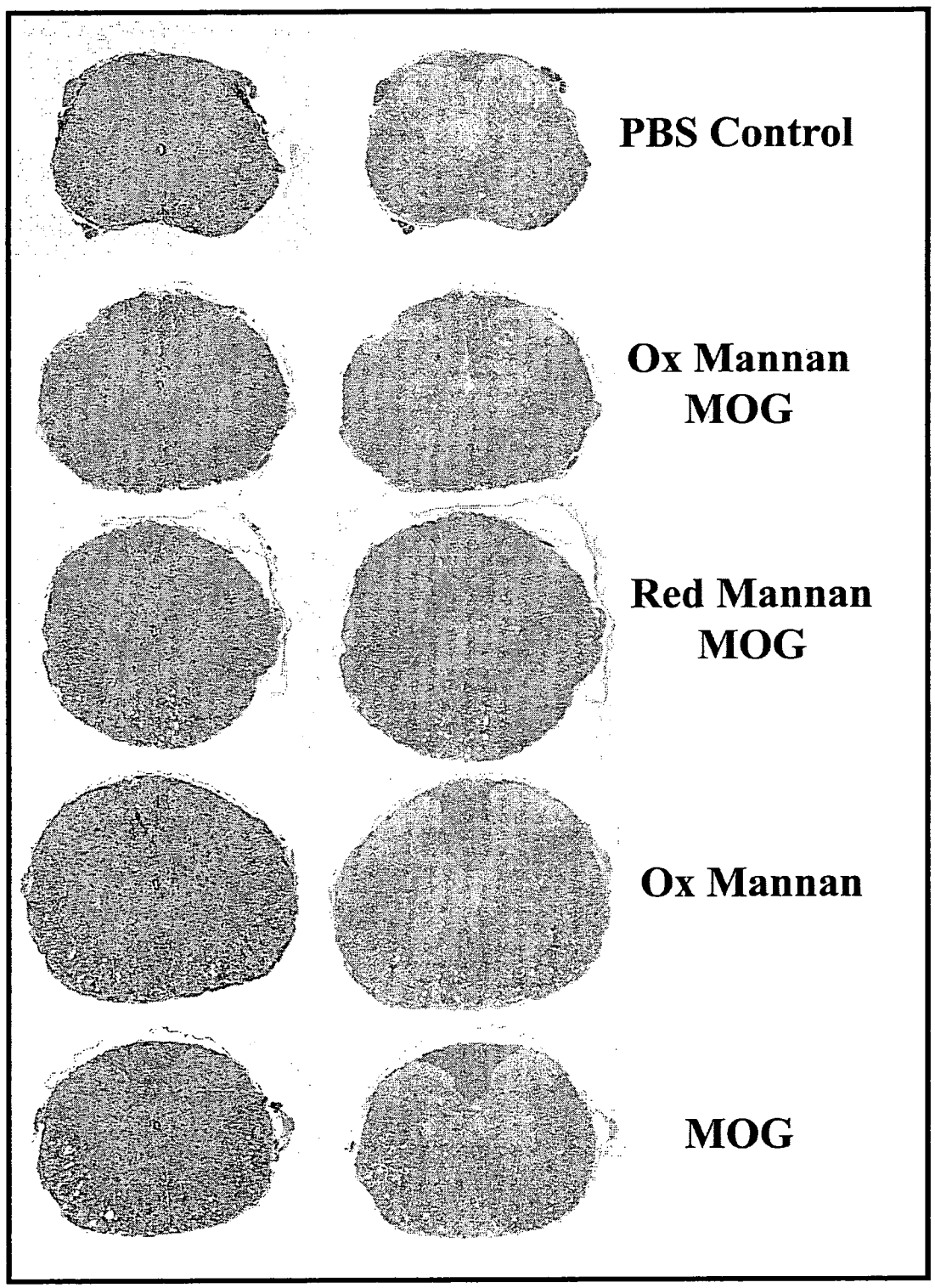
FIG. 5 shows hematoxylin-eosin and luxol fast blue staining of spinal cord sections from the indicated groups of mice to observe inflammatory cell infiltration and demyelination respectively.

Absence of Inflammatory Infiltrates and Demyelinating Lesions in Mice Immunized with Oxidized/Reduced Mannan-$MOG_{35-55}$ Conjugates Prior to EAE Induction Animals were sacrificed 24 days following EAE induction. Spinal cords and brains were examined for the presence of inflammation and demyelination. Evaluation of the extent of lymphocyte infiltration and demyelination (FIG. 5) shows mice that had not received any vaccination had substantial amount of mononuclear cells infiltrating the spinal cord accompanied by extensive demyelination. In contrast, oxidized mannan $MOG_{35-55}$ vaccinated mice showed little inflammatory infiltration and no demyelinating lesions in the spinal cord. Intermediate protective effects were seen in reduced mannan $MOG_{35-55}$ vaccinated mice, $MOG_{35-55}$ peptide and mannan alone were used as controls.

In a detailed examination of the demyelination and inflammation scores for each individual mouse (FIG. 6) the marked reduction in the inflammatory and demyelination index for the oxidized mannan $MOG_{35-55}$ treated mice is observed for both brain and spinal cord. This analysis provides strong pathophysiological evidence in support of a therapeutic nature of the vaccination with the $MOG_{35-55}$ mannan conjugates.

Decreased Proliferative T Cell Responses in Mice Immunized with Oxidized/Reduced Mannan $MOG_{35-55}$ Peptide Conjugates Following $MOG_{35-55}$-EAE Induction Splenocytes were isolated from animals on day 25 post $MOG_{35-55}$-EAE induction. Single cell suspensions were ex vivo stimulated in triplicate with increasing concentrations of $MOG_{35-55}$ peptide. Proliferation was assessed by [$^3$H]-thymidine incorporation. Significant reduced proliferation was noted in spleens from mice that were pre-immunized with oxidized/reduced mannan-$MOG_{35-55}$ peptide conjugates (FIG. 7), compared to mice that had received oxidized mannan alone, reduced mannan alone or control (PBS), prior to $MOG_{35-55}$-EAE induction (FIG. 7). At 100 μg/ml $MOG_{35-55}$ recall peptide, T cell proliferation peaked with a stimulation index of 7 compared to a stimulation index of 3 (in mannan-peptide immunized group) (FIG. 7). Likewise, immunization with $MOG_{35-55}$ peptide alone or control mice (PBS) did not show a reduction in T cell proliferative responses (FIG. 8). The results indicate that the presence of oxidized or reduced mannan in the peptide conjugates is able to tolerize (down-regulate) T cell responses to self peptides.

Cytokine Release from Spleens of Vaccinated Mice

Splenocytes were isolated from C57BL/6 mice on day 25 post MOG$_{35-55}$-EAE induction. Single cell suspensions were stimulated ex vivo in triplicate wells with 10 µg/ml MOG$_{35-55}$ peptide. Supernatants were collected and subjected to a bead-based flow cytometric assay for measurement of Th1/Th2 cytokines. Results shown are for IFN-γ, TNF-α and IL-2. Since IL-17 production has also been implicated in the effector phase of EAE and has recently been shown to play important role in disease development and progression [Sutton, et al., 2006; Komiyama, et al., 2006], we also measured IL-17 production using a commercially available ELISA kit. Overall protective vaccination with reduced or oxidized mannan-MOG$_{35-55}$ peptide conjugates induced reduction in the levels of Th1 cytokines and in the amount of IL-17 secreted by the MOG$_{35-55}$ specific T cells. The results that reached a level of significance with p values <0.05 are hightlighted in FIG. 9.

Vaccination with Oxidized/Reduced Mannan-PLP$_{139-151}$ Peptide Conjugates Protect SJL/J Mice Against PLP$_{139-151}$-EAE Female mice were injected with oxidized/reduced mannan alone or oxidized/reduced mannan-PLP$_{139-151}$ conjugates, with three consecutive immunizations. On day 24 mice were challenge with EAE, in order to test the protective efficacy of oxidized/reduced mannan conjugated peptides. Mice vaccinated with reduced mannan alone or control mice (non immunized) induced severe EAE clinical signs with clinical score up to, 4, Mice immunized with oxidized mannan induced less severe EAE with the peak clinical score of 2.5 (FIG. 10). Interestingly, both of the groups of mice immunized with oxidized or reduced mannan-PLP$_{139-151}$ conjugates did not induce EAE (clinical score 0.5, weight loss), thus indicating that the use of mannan conjugates with the encepahalitogenic PLP$_{139-151}$ peptide could protect mice from inducing EAE (FIG. 10).

Vaccination with Oxidized/Reduced Mannan-MBP$_{83-99}$ Peptide Conjugates Inhibits MBP$_{74-85}$-EAE in Lewis Rats Lewis rats were used as an alternative species to test the therapeutic efficacy of oxidized/reduced mannan conjugated peptides in the treatment of EAE. For this series of experiments Lewis rats received three consecutive vaccinations with mannan in reduced or oxidized form conjugated to MPB$_{83-99}$ peptide spaced 15 days apart, including the necessary control groups that received mannan alone in the reduced or oxidized form. Induction of EAE in Lewis rats was done using the MBP$_{74-85}$ peptide. Clinical scoring (FIG. 11) of the experimental animals and weight monitoring (FIG. 12) showed similar protective findings in that, vaccination with oxidized/reduced mannan MBP$_{83-99}$ conjugates protected Lewis rats from EAE, delaying disease onset by 5 days and lowering the mean clinical severity of disease.

Various modifications and variations of the described aspects of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes of carrying out the invention which are obvious to those skilled in the relevant fields are intended to be within the scope of the following claims.

REFERENCES

Acres, B.; Apostolopoulos, V.; Balloul, J. M.; Wreschner, D.; Xing, P. X.; Ali-Hadji, D.; Bizouarne, N.; Kieny, M. P.; McKenzie, I. F. *Cancer Immunol Immunother,* 2000, 48, 588;

Apostolopoulos, V.; Pietersz, A.; McKenzie, I. *Vaccine,* 1996, 14, 930;

Apostolopoulos, V.; McKenzie, I. F.; Pietersz, G. A. *Immunology and cell biology,* 1996, 74, 457;

Apostolopoulos, V.; Barnes, N.; Pietersz, G. A.; McKenzie, I. F. *Vaccine,* 2000a, 18, 3174;

Apostolopoulos, V.; Pietersz, G. A.; Gordon, S.; Martinez-Pomares, L.; McKenzie, I. F. *European journal of immunology,* 2000b, 30, 1714-1723;

Davis, W. C.; Konzek, R. L.; Haas, K.; Estes, D. M.; Hamilton, M. J.; Call, D. R.; Apostolopoulos, V.; McKenzie, I. F. *Annals of the New York Academy of Sciences,* 2002, 969, 119;

Komiyama Y.; Nakae S.; Matsuki T.; Nambu A.; Ishigame H.; Kakuta S.; Sudo K.; Iwakura Y. *J Immunol,* 2006, 177(1): 566;

Kuchroo, V. K.; R. A. Sobel, J. C.; Laning, C. A.; Martin, E.; Greenfield, M. E.; Dorf, and M. B. Lees. *J Immunol,* 1992, 148:3776;

Kuchroo, V. K.; J. M. Greer, D.; Kaul, G.; Ishioka, A.; Franco, A.; Sette, R. A. Sobel, and M. B. Lees. *J Immunol,* 1994, 153:3326;

Linington, C.; Bradl, M.; Lassmann, H.; Brunner, C.; Vass, K. *The American journal of pathology,* 1988, 130, 443;

Lees, C. J.; Apostolopoulos, V.; Acres, B.; Ong, C. S.; Popovski, V.; McKenzie, I. F. *Cancer Immunol Immunother,* 2000a, 48, 644;

Lees, C. J.; Apostolopoulos, V.; Acres, B.; Ramshaw, I.; Ramsay, A.; Ong, C. S.; McKenzie, I. F. *Vaccine,* 2000b, 19, 158;

Lees, C. J., Apostolopoulos, V., and McKenzie, I. F. *J Interferon Cytokine Res,* 1999, 19, 1373;

Martin, R.; McFarland, H.; McFarlin, D. *Ann. Rev. Immunol.* 1992, 10, 153;

Greer, J. M; Scurses, P. A; Cameron, K. D.; McCombe, P. A; Good, M. F.; Pender, M. P. *Brain* 1997, 120(8): 1447;

Singh, R. A. K.; Zhang, J. Z. *The Journal of Immunology,* 2004, 173:7299;

Greer J. M.; Csurhes P. A; Pender, M. P.; McCombe, P. A. *Journal of Autoimmunity* 2004 22 (4) 345;

Tsuchida, T.; Parker, K. C.; Turner, R. V.; McFarland, H. F.; Coligan, J. E.; Biddison, W. E. *Proc. Natl. Acad. Sci.* 1994, 91:10859;

Trotter, J. L.; Perfrey, C C. M.; Trotter, A. L.; Selvidge, J. A.; Gushleff, K. C.; Mohanakumar, T.; McFarland, H. F. *Journal of Neuroimmunology* 1998, 84, 172;

Mantzourani E. D.; Platts J. A.; Brancale A.; Mavromoustakos T. M.; Tselios T. V. *Journal of Molecular Graphics and Modelling* 2007, 26(2), 471;

McFarlin, D. E.; Blank, S. E.; Kibler, R. F.; McKneally, S.; Shapira, R. *Science,* 1973, 179, 478;

Mendel, I.; Kerlero de Rosbo, N.; Ben-Nun, A. *European journal of immunology,* 1995, 25, 1951;

Steinman, L. *Cell* 1996, 85, 299;

Sutton, C.; Brereton, C.; Keogh, B.; Mills, K. H.; Lavelle, E C. *J Exp Med.* 2006, 203(7):1685;

Tselios, T.; Probert, L.; Daliani, I.; Matsoukas, E.; Troganis, A.; Gerothanasis, I.; Mavromoustakos T.; Moore G.; Matsoukas J. *J. Med. Chem.,* 1999, 42, 7:1170;

Tselios, T.; Daliani, I.; Probert, L.; Deraos, S.; Matsoukas, E.; Roy, S.; Pires, J.; Moore, G.; Matsoukas, J. *Bioorg. Med. Chem.,* 2000a, 8: 1903;

Tselios, T.; Daliani, I.; Deraos, S.; Thymianou, S.; Matsoukas, E.; Troganis, A.; Gerothanassis, I.; Mouzaki, A.; Mavromoustakos, T.; Probert, L.; Matsoukas, J. *Bioorg. Med. Chem. Lett.,* 2000b, 10: 2713;

Tselios, T.; Apostolopoulos, V.; Daliani, I.; Deraos, S.; Grdadolnik, S.; Mavromoustakos, T.; Melachrinou, M.; Thymianou, S.; Probert, L.; Mouzaki, A.; Matsoukas, J. *J. Med. Chem.* 2002, 45, 275;

Matsoukas, J.; Apostolopoulos, V.; Kalbacher, H.; Papini, A. M.; Tselios, T.; Chatzantoni, K.; Biagioli, T.; Lolli, F.; Deraos, S.; Papathanassopoulos, P.; Troganis, A.; Mantzourani, E.; Mavromoustakos, T.; Mouzaki, A. *J Med Chem.* 2005 Mar. 10, 48(5):1470;

Mantzourani, E. D.; Mavromoustakos, T. M.; Platts, J. A.; Matsoukas, J. M.; Tselios, T. V. *Cur. Med. Chem.* 2005, 12, 13, 1569;

Tselios, T. V.; Lamari, F. N.; Karathanasopoulou, I.; Katsara, M.; Apostolopoulos, V.; Pietersz, G. A.; Matsoukas, J. M.; Karamanos, N. K. *Anal Biochem.* 2005, 1; 347(1): 121;

Mantzourani, E.; Tselios T.; Grdadolnik, S. G.; Brancale, A.; Matsoukas, J.; Mavromoustakos T. *Journal of Molecular Graphics and Modelling* 2006a, 25/1, 17;

Mantzourani, E. D.; Tselios, T. V.; Golič Grdadolnik, S.; Platts, J. A.; Brancale, A.; Deraos, G.; Matsoukas, J. M.; Mavromoustakos, T. M. *J. Med. Chem.* 2006b, 49, 6683;

Vaughan, H. A.; Ho, D. W.; Karanikas, V.; Sandrin, M. S.; McKenzie, I. F.; Pietersz, G. A. *Vaccine,* 2000, 18, 3297;

Vaughan, H. A.; Ho, D. W.; Karanikas, V. A.; Ong, C. S.; Hwang, L. A.; Pearson, J. M.; McKenzie, I. F.; Pietersz, G. A. *Vaccine,* 1999, 17, 2740;

Zamvil, S S. and Steinman, L. *Annu Rev Immunol.* 1990, 8, 579;

The invention claimed is:

1. A conjugate comprising:
   (i) mannan; and
   (ii) a peptide fragment of myelin oligodentrocyte glycoprotein (MOG) in linear or cyclic form;
   wherein said peptide fragment is linked to mannan via a [(Lys-Gly)$_n$] bridge, where n is an integer from 1 to 10;
   wherein the peptide fragment comprises an immunodominant epitope selected from MOG$_{35-55}$ and MOG$_{97-108}$, in linear or c 2. A conjugate according to claim 1 wherein the peptide fragment comprises the peptide $MOG_{35-55}$, in linear or cyclic form.

3. A conjugate according to claim 1 wherein the mannan is reduced mannan.

4. A conjugate according to claim 1 wherein the mannan is oxidized mannan.

5. A conjugate according to claim 1 wherein two or more peptide fragments, or cyclic counterparts thereof, are linked to mannan.

6. A conjugate according to claim 5 wherein the peptide fragments (or cyclic counterparts thereof) are different.

7. A mixture comprising two or more conjugates according to claim 1.

8. A mixture according to claim 7 wherein the conjugates are different.

9. A pharmaceutical preparation comprising a conjugate according to claim 1, and a pharmaceutically acceptable carrier, diluent or excipient.

10. A process for preparing a conjugate according to claim 1, said process comprising the steps of:
   (i) reacting an epitope comprising a peptide fragment of the myelin oligodentrocyte glycoprotein (MOG), said MOG fragment being in linear or cyclic form, with a peptide bridge $[(Lys-Gly)_n]$, wherein n is an integer from 1 to 10;
   (ii) reacting the product formed in step (i) with oxidized mannan; and
   (iii) optionally reducing the product formed in step (ii) to form a reduced mannan conjugate.

11. A vaccine comprising a conjugate according to claim 1.

12. A conjugate of claim 1 further comprising:
   (ii)(a) an epitope comprising a peptide fragment of myelin basic protein (MBP);
   (ii)(b) an epitope comprising a peptide fragment of myelin oligodentrocyte glycoprotein (MOG); and
   (ii)(c) an epitope comprising a peptide fragment of proteolipid protein (PLP);
   each peptide fragment being in linear or cyclic form.

13. The conjugate of claim 5, wherein the conjugate comprises
   (i) a peptide fragment of myelin oligodentrocyte glycoprotein (MOG); and
   (ii) one of
      (a) a peptide fragment of myelin basic protein (MBP); and
      (b) a peptide fragment of proteolipid protein (PLP).

14. A conjugate according to claim 1 wherein the peptide fragment consists of the peptide of SEQ ID NO. 2: H-Met-Glu-Val-Gly-Trp-Tyr-Arg-Pro-Pro-Phe-Ser-Arg-Val-Val-His-Leu-Tyr-Arg-Asn-Gly-Lys-OH [SEQ ID NO. 2] in linear or cyclic form.

15. A conjugate according to claim 14 wherein the peptide fragment is linked to mannan via a $[(Lys-Gly)_5]$ bridge.

* * * * *

SEQUENCE LISTING

```
<160> NUMBER OF SEQ ID NOS: 26

<210> SEQ ID NO 1
<211> LENGTH: 17
<212> TYPE: PRT
<213> ORGANISM: Homo sapiens
<220> FEATURE:
<221> NAME/KEY: MISC_FEATURE
<223> OTHER INFORMATION: Peptide can be linear or cyclic

<400> SEQUENCE: 1

Glu Asn Pro Val Val His Phe Phe Lys Asn Ile Val Thr Pro Arg Thr
1               5                   10                  15

Pro

<210> SEQ ID NO 2
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide can be linear or cyclic
<220> FEATURE:
<221> NAME/KEY: MISC_FEATURE
<222> LOCATION: (8)..(8)
<223> OTHER INFORMATION: Xaa may be Pro or Ser

<400> SEQUENCE: 2

Met Glu Val Gly Trp Tyr Arg Xaa Pro Phe Ser Arg Val Val His Leu
1               5                   10                  15

Tyr Arg Asn Gly Lys
            20

<210> SEQ ID NO 3
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide can be linear or cyclic

<400> SEQUENCE: 3

His Ser Leu Gly Lys Trp Leu Gly His Pro Asp Lys Phe
1               5                   10

<210> SEQ ID NO 4
```

```
<211> LENGTH: 25
<212> TYPE: PRT
<213> ORGANISM: Homo sapiens

<400> SEQUENCE: 4

Gln Asp Glu Asn Pro Val Val His Phe Phe Lys Asn Ile Val Thr Pro
1               5                   10                  15

Arg Thr Pro Pro Pro Ser Gln Gly Lys
            20                  25

<210> SEQ ID NO 5
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide can be linear or cyclic
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 5

Glu Asn Pro Val Val His Phe Phe Xaa Asn Ile Val Thr Xaa Arg Thr
1               5                   10                  15

Pro

<210> SEQ ID NO 6
<211> LENGTH: 13
<212> TYPE: PRT
<213> ORGANISM: Homo sapiens

<400> SEQUENCE: 6

His Ser Leu Gly Lys Trp Leu Gly His Pro Asp Lys Phe
1               5                   10

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<223> OTHER INFORMATION: Peptide can be linear or cyclic
<220> FEATURE:
<221> NAME/KEY: MISC_FEATURE
<222> LOCATION: (9)..(9)
<223> OTHER INFORMATION: Xaa can be Ala, Arg, Glu, Phe, Ser or Tyr
<220> FEATURE:
<221> NAME/KEY: MISC_FEATURE
<222> LOCATION: (14)..(14)
<223> OTHER INFORMATION: Xaa can be Ala, Arg, Glu, Phe or Tyr

<400> SEQUENCE: 7

Glu Asn Pro Val Val His Phe Phe Xaa Asn Ile Val Thr Xaa Arg Thr
1               5                   10                  15

Pro

<210> SEQ ID NO 8
<211> LENGTH: 13
<212> TYPE: PRT
```

```
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(5)
<223> OTHER INFORMATION: Xaa can be Lys, Ala or Arg
<220> FEATURE:
<221> NAME/KEY: MISC_FEATURE
<222> LOCATION: (10)..(10)
<223> OTHER INFORMATION: Xaa can be Pro or Ala

<400> SEQUENCE: 8

Val His Phe Phe Xaa Asn Ile Val Thr Xaa Arg Thr Pro
1               5                   10

<210> SEQ ID NO 9
<211> LENGTH: 27
<212> TYPE: PRT
<213> ORGANISM: Artificial Sequence
<220> FEATURE:
<223> OTHER INFORMATION: Synthetic peptide

<400> SEQUENCE: 9

Lys Gly Lys Gly Lys Gly Lys Gly Lys Gly Glu Asn Pro Val Val His
1               5                   10                  15

Phe Phe Lys Asn Ile Val Thr Pro Arg Thr Pro
            20                  25

<210> SEQ ID NO 10
<211> LENGTH: 23
<212> TYPE: PRT
<213> ORGANISM: Artificial Sequence
<220> FEATURE:
<223> OTHER INFORMATION: Synthetic peptide

<400> SEQUENCE: 10

Lys Gly Lys Gly Lys Gly Lys Gly Lys Gly His Ser Leu Gly Lys Trp
1               5                   10                  15

Leu Gly His Pro Asp Lys Phe
            20

<210> SEQ ID NO 11
<211> LENGTH: 31
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (18)..(18)
<223> OTHER INFORMATION: Xaa may be Pro or Ser

<400> SEQUENCE: 11

Lys Gly Lys Gly Lys Gly Lys Gly Lys Gly Met Glu Val Gly Trp Tyr
1               5                   10                  15

Arg Xaa Pro Phe Ser Arg Val Val His Leu Tyr Arg Asn Gly Lys
            20                  25                  30

<210> SEQ ID NO 12
<211> LENGTH: 17
<212> TYPE: PRT
<213> ORGANISM: Artificial Sequence
<220> FEATURE:
<223> OTHER INFORMATION: Synthetic peptide; [R91,A96]MBP83-99
<220> FEATURE:
<221> NAME/KEY: MISC_FEATURE
<223> OTHER INFORMATION: Peptide can be linear or cyclic
```

<400> SEQUENCE: 12

Glu Asn Pro Val Val His Phe Phe Arg Asn Ile Val Thr Ala Arg Thr
1               5                   10                  15

Pro

<210> SEQ ID NO 13
<211> LENGTH: 17
<212> TYPE: PRT
<213> ORGANISM: Artificial Sequence
<220> FEATURE:
<223> OTHER INFORMATION: Synthetic peptide; [A91,A96]MBP83-99
<220> FEATURE:
<221> NAME/KEY: MISC_FEATURE
<223> OTHER INFORMATION: Peptide can be linear or cyclic

<400> SEQUENCE: 13

Glu Asn Pro Val Val His Phe Phe Ala Asn Ile Val Thr Ala Arg Thr
1               5                   10                  15

Pro

<210> SEQ ID NO 14
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa can be Arg, Glu, Phe, and Tyr
<220> FEATURE:
<221> NAME/KEY: MISC_FEATURE
<222> LOCATION: (14)..(14)
<223> OTHER INFORMATION: Xaa can be Arg, Glu, Phe, and Tyr

<400> SEQUENCE: 14

Glu Asn Pro Val Val His Phe Phe Xaa Asn Ile Val Thr Xaa Arg Thr
1               5                   10                  15

Pro

<210> SEQ ID NO 15
<211> LENGTH: 17
<212> TYPE: PRT
<213> ORGANISM: Artificial Sequence
<220> FEATURE:
<223> OTHER INFORMATION: Synthetic peptide; [E91]MBP83-99

<400> SEQUENCE: 15

Glu Asn Pro Val Val His Phe Phe Glu Asn Ile Val Thr Pro Arg Thr
1               5                   10                  15

Pro

<210> SEQ ID NO 16
<211> LENGTH: 17
<212> TYPE: PRT
<213> ORGANISM: Artificial Sequence
<220> FEATURE:
<223> OTHER INFORMATION: Synthetic peptide; [F91]MBP83-99

<400> SEQUENCE: 16

Glu Asn Pro Val Val His Phe Phe Phe Asn Ile Val Thr Pro Arg Thr
1               5                   10                  15

Pro

<210> SEQ ID NO 17
<211> LENGTH: 17
<212> TYPE: PRT
<213> ORGANISM: Artificial Sequence
<220> FEATURE:
<223> OTHER INFORMATION: Synthetic peptide; [Y91]MBP83-99

<400> SEQUENCE: 17

Glu Asn Pro Val Val His Phe Phe Tyr Asn Ile Val Thr Pro Arg Thr
1               5                   10                  15

Pro

<210> SEQ ID NO 18
<211> LENGTH: 17
<212> TYPE: PRT
<213> ORGANISM: Artificial Sequence
<220> FEATURE:
<223> OTHER INFORMATION: Synthetic peptide; [A91]MBP83-99
<220> FEATURE:
<221> NAME/KEY: MISC_FEATURE
<223> OTHER INFORMATION: Peptide can be linear or cyclic

<400> SEQUENCE: 18

Glu Asn Pro Val Val His Phe Phe Ala Asn Ile Val Thr Pro Arg Thr
1               5                   10                  15

Pro

<210> SEQ ID NO 19
<211> LENGTH: 17
<212> TYPE: PRT
<213> ORGANISM: Artificial Sequence
<220> FEATURE:
<223> OTHER INFORMATION: Synthetic peptide; cyclo(83-99)[R91]MBP83-99

<400> SEQUENCE: 19

Glu Asn Pro Val Val His Phe Phe Arg Asn Ile Val Thr Pro Arg Thr
1               5                   10                  15

Pro

<210> SEQ ID NO 20
<211> LENGTH: 17
<212> TYPE: PRT
<213> ORGANISM: Artificial Sequence
<220> FEATURE:
<223> OTHER INFORMATION: Synthetic peptide; cyclo(83-99)[F91,
      A96]MBP83-99

<400> SEQUENCE: 20

Glu Asn Pro Val Val His Phe Phe Phe Asn Ile Val Thr Ala Arg Thr
1               5                   10                  15

Pro

<210> SEQ ID NO 21
<211> LENGTH: 17
<212> TYPE: PRT
<213> ORGANISM: Artificial Sequence
<220> FEATURE:
<223> OTHER INFORMATION: Synthetic peptide; cyclo(83-99)[Y91,
      A96]MBP83-99

<400> SEQUENCE: 21

Glu Asn Pro Val Val His Phe Phe Tyr Asn Ile Val Thr Ala Arg Thr
1               5                   10                  15

Pro

```
<210> SEQ ID NO 22
<211> LENGTH: 17
<212> TYPE: PRT
<213> ORGANISM: Artificial Sequence
<220> FEATURE:
<223> OTHER INFORMATION: Synthetic peptide; cyclo(83-99)[S91,
    A96]MBP83-99

<400> SEQUENCE: 22

Glu Asn Pro Val Val His Phe Phe Ser Asn Ile Val Thr Ala Arg Thr
1               5                   10                  15

Pro

<210> SEQ ID NO 23
<211> LENGTH: 13
<212> TYPE: PRT
<213> ORGANISM: Artificial Sequence
<220> FEATURE:
<223> OTHER INFORMATION: Synthetic peptide

<400> SEQUENCE: 23

Val His Phe Phe Lys Asn Ile Val Thr Pro Arg Thr Pro
1               5                   10

<210> SEQ ID NO 24
<211> LENGTH: 13
<212> TYPE: PRT
<213> ORGANISM: Artificial Sequence
<220> FEATURE:
<223> OTHER INFORMATION: Synthetic peptide

<400> SEQUENCE: 24

Val His Phe Phe Ala Asn Ile Val Thr Ala Arg Thr Pro
1               5                   10

<210> SEQ ID NO 25
<211> LENGTH: 17
<212> TYPE: PRT
<213> ORGANISM: Artificial Sequence
<220> FEATURE:
<223> OTHER INFORMATION: Synthetic peptide; Cyclo(91-99)[Ala96]
    MBP83-99

<400> SEQUENCE: 25

Glu Asn Pro Val Val His Phe Phe Lys Asn Ile Val Thr Ala Arg Thr
1               5                   10                  15

Pro

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide; [R91, A96]MBP87-99

<400> SEQUENCE: 26

Val His Phe Phe Arg Asn Ile Val Thr Ala Arg Thr Pro
1               5                   10
```